(12) United States Patent
Baltsen et al.

(10) Patent No.: US 10,647,947 B2
(45) Date of Patent: May 12, 2020

(54) DETERGENT COMPOSITION

(71) Applicant: Novozymes A/S, Bagsvaerd (DK)

(72) Inventors: Lilian Eva Tang Baltsen, Bagsvaerd (DK); Kirk Matthew Schnorr, Holte (DK); Klaus Gori, Copenhagen (DK); Lars Kobberoe Skov, Ballerup (DK)

(73) Assignee: Novozymes A/S, Bagsvaerd (DK)

( * ) Notice: Subject to any disclaimer, the term of this patent is extended or adjusted under 35 U.S.C. 154(b) by 30 days.

(21) Appl. No.: 15/315,155

(22) PCT Filed: Jun. 4, 2015

(86) PCT No.: PCT/EP2015/062502
§ 371 (c)(1),
(2) Date: Nov. 30, 2016

(87) PCT Pub. No.: WO2015/185689
PCT Pub. Date: Dec. 10, 2015

(65) Prior Publication Data
US 2018/0216040 A1    Aug. 2, 2018

(30) Foreign Application Priority Data

Jun. 4, 2014    (EP) .................................. 14171164

(51) Int. Cl.
*C11D 3/386*    (2006.01)
*C12N 9/38*    (2006.01)
*C12N 9/24*    (2006.01)

(52) U.S. Cl.
CPC ........ *C11D 3/38636* (2013.01); *C12N 9/2468* (2013.01); *C12Y 302/01164* (2013.01)

(58) Field of Classification Search
None
See application file for complete search history.

(56) References Cited

U.S. PATENT DOCUMENTS 6,329,185 B1    12/2001    Kofod
6,486,112 B1*   11/2002    Bettiol .................. C11D 3/0036
                                                                510/276
2002/0155575 A1* 10/2002    Norregaard-Madsen ...................
                                                                C11D 3/38681
                                                                435/222
2006/0042020 A1    3/2006    Salmon
2008/0221008 A1    9/2008    Mikkelsen
2013/0219568 A1    8/2013    Sweeney

FOREIGN PATENT DOCUMENTS

| CA | 2385300 A1 | 4/2001 |
|---|---|---|
| JP | H04-146998 A | 5/1992 |
| WO | 95/02043 A1 | 1/1995 |
| WO | 01/23534 A1 | 4/2001 |
| WO | 2005/003356 A1 | 1/2005 |
| WO | 2008/057637 A2 | 5/2008 |
| WO | 2010/115021 A2 | 10/2010 |
| WO | 2011/130076 A1 | 10/2011 |
| WO | 2013/092635 A1 | 6/2013 |

OTHER PUBLICATIONS

GenBank Accession No. EHK21040 (Year: 2011).*
Wikipedia entry for Enzyme Commission Number, Retrieved from "https://en.wikipedia.org/w/index.php?title=Enzyme_Commission_number&oldid=873971191" on Mar. 28, 2019 (Year: 2019).*
Kegg Enzyme: 3.2.1.164, retrieved from https://www.genome.jp/dbget-bin/www_bget?ec:3.2.1.164 on Mar. 28, 1929 (Year: 2019).*
D.K.F. Santos et al. "Biosurfactants: Multifunctional Biomolecules of the 21st Century", International J. Mol. Sci. 17:401 (Year: 2016).*
F. Spina et al. "Screening of Anionic Biosurfactants Production among Fungi and Bacteria", Chemical Engineering Transaqctions 64: 493-498. (Year: 2018).*
Anonymous, UniParc Accession No. UPI0002397C68 (2012).
Ulhoa et al, 1992, Enzyme Microb Technol 14(3), 236-240.
Singh et al, 2011, European journal of plant pathology 131(1), 121-134.

* cited by examiner

*Primary Examiner* — Rebecca E Prouty
(74) *Attorney, Agent, or Firm* — Kristin McNamara

(57) ABSTRACT

The present invention concerns a detergent comprising a polypeptide having galactanase activity. It further concerns a laundering method and the use of galactanases. The present invention further relates to polypeptides having galactanase activity, nucleotides encoding the polypeptide, as well as methods of producing the polypeptides.

18 Claims, No Drawings

Specification includes a Sequence Listing.

DETERGENT COMPOSITION

CROSS-REFERENCE TO RELATED APPLICATIONS

This application is a 35 U.S.C. 371 national application of international application no. PCT/EP2015/062502 filed Jun. 4, 2015, which claims priority or the benefit under 35 U.S.C. 119 of European application no. 14171164.8 filed Jun. 4, 2014. The content of each application is fully incorporated herein by reference.

REFERENCE TO A SEQUENCE LISTING

This application contains a Sequence Listing in computer readable form, which is incorporated herein by reference.

FIELD OF THE INVENTION

The present invention concerns a detergent comprising a galactanase. It further concerns a laundering method and the use of galactanases. The present invention further relates to polypeptides having galactanase activity, nucleotides encoding the polypeptide, as well as methods of producing the polypeptides.

BACKGROUND OF INVENTION

Microorganisms generally live attached to surfaces in many natural, industrial, and medical environments, encapsulated by extracellular substances including biopolymers and macromolecules. The resulting layer of slime encapsulated microorganism is termed a biofilm.

Biofilms are the predominant mode of growth of bacteria in the natural environment, and bacteria growing in biofilms exhibit distinct physiological properties. Compared to their planktonically grown counterparts, the bacteria in a biofilm are more resistant to antibiotics, UV irradiation, detergents and the host immune response.

It has for many years been a known problem to remove patches of underarm sweat from shirts and blouses. This stain is very difficult to dissolve and usually consists of a lot of different components. When laundry items like T-shirts or sportswear are used, they are exposed to bacteria from the body of the user and from the rest of the environment in which they are used. Some of these bacteria are capable of adhering to the laundry item and form a biofilm on the item. The presence of bacteria implies that the laundry items become sticky and therefore soil adheres to the sticky areas. This soil has shown difficult to remove by commercially available detergent compositions. Further, when very dirty laundry items are washed together with less dirty laundry items the dirt present in the wash liquor tend to stick to the biofilm. As a result hereof the laundry item is more "soiled" after wash than before wash.

Temperature has a significant influence on dissolving and wiping the components of sweat stain. Inadequate sweat stain removal can lead to discoloration of the area under the arms. This discoloration increases if the laundry is washed with other very dirty clothes. Sportswear is a good example because there is often soil, clay and traffic dirt on the clothes washed together with very sweaty shirts. From wash to wash the sweat stain become more and more colored so they eventually appear as developed spots. This kind of dirt is one reason why people discard their clothes. Although the problem is well known to most garment the problem is very pronounced for mixed fabrics. There is a European political desire to conserve resources for laundry which has led to their adoption of a labeling law for washing machines in the EU to exclude machines with high demand. This means that cold water washing is much more prevalent in the EU and thus come to resemble the rest of the world wash circumstances better. This means that there is a risk that energy consumption moves from wash warm and remove more sweat stain versus discarding clothes and buying new. There is an urgent need to solve the problem of removing sweat stains effectively.

SUMMARY OF THE INVENTION

The present invention concerns a detergent composition comprising a polypeptide having endo-beta-1,6-galactanase activity and a detergent adjunct ingredient.

The invention further concerns a cleaning or laundering method for cleaning or laundering an item comprising the steps of:
  a. Exposing an item to a wash liquor comprising a polypeptide having endo-beta-1,6-galactanase activity or a wash liquor comprising a detergent composition comprising a polypeptide having endo-beta-1,6-galactanase activity;
  b. Completing at least one wash cycle; and
  c. Optionally rinsing the item,
wherein the item is a textile, a dishware or a hard surface In addition, the use of polypeptides having endo-beta-1,6-galactanase activity for preventing, reducing or removing the biofilm of an item is claimed.

The present invention further relates to polypeptide having endo-beta-1,6-galactanase activity, nucleotides encoding the polypeptide and methods of producing the polypeptide.

DEFINITIONS

The term "automatic dishwashing composition" refers to compositions intended for cleaning dishware such as plates, cups, glasses, bowls, cutlery such as spoons, knives, forks, serving utensils, ceramics, plastics, metals, china, glass and acrylics in a dishwashing machine.

The terms encompass any materials/compounds selected for domestic or industrial washing applications and the form of the product can be liquid, powder or granulate. In addition to endo-beta-1,6-galactanase, the automatic dishwashing composition contains detergent components such as enzymes, polymers, bleaching systems, bleach activators, bleach catalysts, silicates, dyestuff and metal care agents.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Biofilm: A biofilm is any group of microorganisms in which cells stick to each other on a surface, such as a textile, dishware or hard surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from free-floating bacteria of the same species, as the dense and protected environment of the film allows them to cooperate and interact in various ways. One benefit of this environment is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis, Corynebacterium xerosis* and *Stenotrophomonas* sp.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Detergent adjunct ingredient: The detergent adjunct ingredient is different to the endo-beta-1,6-galactanase of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aid, chelating agents, dye transfer inhibitors, enzymes, enzyme stabilizers, enzyme inhinitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

Detergent composition: The term "detergent composition" includes, unless otherwise indicated, all forms of detergent compositions such as gel, granulate, liquid, paste, powder, spray or tablet compositions including heavy-duty liquids (HDL), fine-fabric liquid detergents, liquid and/or solid laundry detergents and fine fabric detergents; hard surface cleaning formulations for e.g. glass, wood, ceramic and metal counter tops and windows; carpet cleaners; oven cleaners; fabric fresheners; fabric softeners; textile and laundry pre-spotters, as well as dish wash detergents such as hand dishwashing agents, light duty dishwashing agents, machine dishwashing agents such as automatic dish wash (ADW); all-purpose or heavy-duty washing agents, liquid, gel or paste-form all-purpose washing agents, liquid cleaning and disinfecting agents, including antibacterial handwash types, cleaning bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types. Detergent compositions, include cleaning compositions for laundry, hard surface cleaning, automatic dish wash, manual dish wash, ADW, industrial cleaning, such compositions can be used in cleaning or laundering methods for cleaning or laundering an item, wherein the item is a textile, a dishware or a hard surface.

In addition to containing an endo-beta-1,6-galactanase of the invention, the detergent formulation may contain one or more enzymes (such as proteases, amylases, lipases, cutinases, cellulases, endoglucanases, xyloglucanases, pectinases, pectin lyases, xanthanases, peroxidaes, haloperoxygenases, catalases and mannanases, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

Dishware: The term dish ware is intended to mean any form of kitchen utensil, dinner set or tableware such as but not limited to pans, plates, cops, knives, forks, spoons, porcelain etc.

Dish washing composition: The term "dish washing composition" refers to compositions comprising detergent components, which composition is intended for cleaning dishes, table ware, pots, pans, cutlery and all forms of compositions for cleaning hard surfaces areas in kitchens. The present invention is not restricted to any particular type of dish wash composition or any particular detergent.

Endo-beta-1,6-galactanase: The term "endo-beta-1,6-galactanase" or "a polypeptide having endo-beta-1,6-galactanase activity" means a endo-beta-1,6-galactanase activity (EC 3.2.1.164) that catalyzes the hydrolytic cleavage of 1,6-β-D-galactooligosaccharides with a degree of polymerization (DP) higher than 3, and their acidic derivatives with 4-O-methylglucosyluronate or glucosyluronate groups at the non-reducing terminals. For purposes of the present invention, endo-beta-1,6-galactanase activity is determined according to the procedure described in Assay I. In one aspect, the polypeptides of the present invention have at least 20%, e.g., at least 40%, at least 50%, at least 60%, at least 70%, at least 80%, at least 90%, at least 95%, or at least 100% of the endo-beta-1,6-galactanase activity of the mature polypeptide of SEQ ID NO: 2. The two terms polypeptide having Endo-beta-1,6-galactanase activity and Endo-beta-1,6-galactanase are used interchangeably.

Enzyme Detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and/or cleaning, prevention or reduction of redeposition of soils released in the washing process (an effect that also is termed anti-redeposition), restoring fully or partly the whiteness of textiles which originally were white but after repeated use and wash have obtained a greyish or yellowish appearance (an effect that also is termed whitening). Textile care benefits, which are not directly related to catalytic stain removal or prevention of redeposition of soils, are also important for enzyme detergency benefits. Examples of such textile care benefits are prevention or reduction of dye transfer from one fabric to another fabric or another part of the same fabric (an effect that is also termed dye transfer inhibition or anti-backstaining), removal of protruding or broken fibers from a fabric surface to decrease pilling tendencies or remove already existing pills or fuzz (an effect that also is termed anti-pilling), improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching components such as hydrogen peroxide or other peroxides.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide; wherein the fragment has endo-beta-1,6-galactanase activity. In one aspect, a fragment contains at least 438 amino acid residues (e.g., amino acids 11 to 448 of SEQ ID NO: 2).

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). The term includes both domestic and industrial cleaning applications.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved wash performance: The term "improved wash performance" is defined herein as an enzyme displaying an increased wash performance in a detergent composition relative to the wash performance of same detergent composition without the enzyme e.g. by increased stain removal or less redeposition. The term "improved wash performance" includes wash performance in laundry but also e.g. in hard surface cleaning such as automated dish wash (ADW).

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Laundering: The term "laundering" or "washing" relates to both household laundering and industrial laundering and means the process of treating textiles with a solution containing a cleaning or detergent composition of the present invention. The laundering process can for example be carried out using e.g. a household or an industrial washing machine or can be carried out by hand.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 458 of SEQ ID NO: 2. Amino acids −20 to −1 of SEQ ID NO: 2 are a signal peptide. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having endo-beta-1,6-galactanase activity. In one aspect, the mature polypeptide coding sequence is nucleotides 61 to 1434 of SEQ ID NO: 1 and nucleotides 1 to 60 of SEQ ID NO: 1 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Stringency Conditions:

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.]

Subsequence: The term "subsequence" means a polynucleotide having one or more (e.g., several) nucleotides absent from the 5' and/or 3' end of a mature polypeptide coding sequence; wherein the subsequence encodes a fragment having endo-beta-1,6-galactanase activity. In one aspect, a subsequence contains at least 438 nucleotides (e.g., nucleotides 11 to 448 of SEQ ID NO: 1).

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). Fabric may be conventional washable laundry, for example stained household laundry. When the term fabric or garment is used it is intended to include the broader term textiles as well.

Variant: The term "variant" means a polypeptide having endo-beta-1,6-galactanase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position Wash cycle: The term "wash cycle" is defined herein as a washing operation wherein textile, hard surface or dishware are contacted to a wash liquor, mechanical action of some kind is applied to the textile, hard surface or dishware in order to release stains and to facilitate flow of wash liquor in and out of the textile or on the hard surface/dishware and finally the superfluous wash liquor is removed. After one or more wash cycles, the textile, hard surface or dishware is generally rinsed and dried. For dishwashing the term wash cycle also refers to a washing operation wherein dishware are exposed to the wash liquor for a period of time by circulating the wash liquor and spraying the wash liquor onto the dishware in order to clean the dishware and finally the superfluous wash liquor is removed. A wash cycle may be repeated one, two, three, four, five or even six times at the same or at different temperatures. Hereafter the dishware is generally rinsed and dried. One of the wash cycles can be a soaking step, where the textile, hard surface or dishware is left soaking in the wash liquor for a period.

Wash liquor: The term "wash liquor" is intended to mean the solution or mixture of water and detergents optionally including the polypeptide of the invention.

Whiteness: The term "Whiteness" is a broad term with different meanings in different regions and for different consumers. Loss of whiteness can e.g. be due to greying, yellowing, or removal of optical brighteners/hueing agents. Greying and yellowing can be due to soil redeposition, body soils, colouring from e.g. iron and copper ions or dye transfer. The term whiteness as define herein includes one or several issues from the list below: colourant or dye effects; incomplete stain removal (e.g. body soils, sebum etc.); redeposition (greying, yellowing or other discolourations of the object) (removed soils reassociate with other parts of textile, soiled or unsoiled); chemical changes in textile during application; and clarification or brightening of colours.

DETAILED DESCRIPTION OF THE INVENTION

The inventors have found that polypeptides having endo-beta-1,6-galactanase activity can be used for preventing, reducing or removing biofilm on items such as textile, dishware or hard surfaces.

Biofilm can develop on items when microorganisms are present on the item and sticks together on the item. Some microorganisms tend to adhere to the surface of items such as textiles. Some microorganisms adhere to such surfaces and form a biofilm on the surface. The biofilm may be sticky and the adhered microorganisms and/or the biofilm are difficult to remove. Furthermore the biofilm adhere soil due to the sticky nature of the biofilm. The commercial laundry detergent compositions available on the marked do not effectively remove such adhered microorganisms or biofilm from textile, dishware or hard surfaces.

The present invention concerns the use of a polypeptide having endo-beta-1,6-galactanase activity for preventing, reducing or removing a biofilm of an item, wherein the item is a textile, a dishware or a hard surface. In one embodiment of the invention the polypeptide having endo-beta-1,6-galactanase activity is used for preventing, reducing or removing the stickiness of an item. Stickiness could also be described as gluing or glueness and is the phenomenon of adhering of soil particles to surfaces such as textile. The ability to glue dirt to the surface is a typical phenomenon for most biofilms whether it is situation on textile or other types of surfaces. This gluing effect is a major reason for built up of undefined dirt on surfaces and gives rise to dis coloration of the surfaces. The polypeptide having endo-beta-1,6-galactanase activity can further be used for pretreating biofilm stains on textile, dishware or hard surfaces such as items with a pronounced amount of biofilm adhered to the item. When items like T-shirts or sportswear are used, they are, in addition to sweat, exposed to bacteria from the body of the user and from the rest of the environment in which the T-shirt or sportswear are used. The polypeptide having endo-beta-1,6-galactanase activity is capable of preventing, reducing or removing the adherence of soil to the garment.

Additionally the invention concerns the use of a polypeptide having endo-beta-1,6-galactanase activity for preventing, reducing or removing redeposition of soil during a wash cycle. When the polypeptide is used for example in the laundering of textile, the polypeptide hinders deposition of soil present in the wash liquor to deposit on the textile.

Further, the invention concerns the use of a polypeptide having endo-beta-1,6-galactanase activity for preventing, reducing or removing the adherence of soil to an item. In one embodiment the item is textile. When the soil does not adhere to the item for example a textile, the textile appears more white and clean. Thus, the invention further concerns the use of a polypeptide having endo-beta-1,6-galactanase activity for maintaining or improving the whiteness of an item.

In one embodiment of the invention, the polypeptide having endo-beta-1, 6-galactanase activity improves whiteness of an item, such as a textile. In one embodiment the polypeptide of the invention having endo-beta-1,6-galactanase activity helps maintaining the colour on textiles. When textiles are repeatedly washed the colours tend to be less bright. In one embodiment a polypeptide of the invention having endo-beta-1,6-galactanase has an improved effect of maintaining the colour of coloured textiles even after repeated washes. In one embodiment the polypeptide of the invention also reduced the colouring of non-coloured part of the same or additional textile present in the wash.

The inventors have found that using the polypeptide having endo-beta-1,6-galactanase activity together with a bleaching system, the whiteness of the item is further improved. The bleaching system can be selected from the group consisting of tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), 6-(phthalimido) peroxyhexanoic acid (PAP), NaHCO$_3$ and/or mixtures thereof. In a preferred embodiment the bleaching system comprises tetraacetylethylenediamine (TAED) and NaHCO$_3$.

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds, such as iron or cobalt complexes. In one embodiment, the bleaching comprises a bleach catalyst selected from the group consisting of organic catalysts having the following formulae:

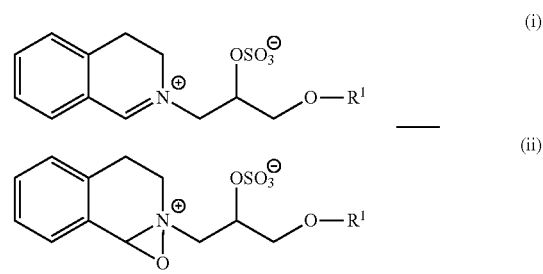

(iii) and mixtures thereof;
wherein each R1 is independently a branched alkyl group containing from 9 to 24 carbons or linear alkyl group containing from 11 to 24 carbons, where each R1 is independently a branched alkyl group containing from 9 to 18 carbons or linear alkyl group containing from 11 to 18 carbons, or where each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

The present invention further concerns a detergent composition comprising a polypeptide having endo-beta-1,6-galactanase activity and a detergent adjunct ingredient. The present detergent composition can be used for preventing, reducing or removing biofilm from an item, for preventing, reducing or removing the stickiness of an item, for pretreating stains on the item, for preventing, reducing or removing redeposition of soil during a wash cycle, for reducing or removing adherence of soil to an item, for maintaining or improving the whiteness of an item and for preventing, reducing or removing malodor from an item. The present detergent composition overcomes the problems of the prior art.

The inventors have surprisingly found that when polypeptides having endo-beta-1,6-galactanase activity are used together with protease, the protease boosts the polypeptide having endo-beta-1,6-galactanase activity, meaning that wash performance of the polypeptide having endo-beta-1, 6-galactanase activity is improved.

Preferred proteases may be an alkaline protease, such as a serine protease. Preferred proteases includes BPN', subtilisin Novo, subtilisin Carlsberg, subtilisin 309, subtilisin 147, subtilisin 168. Other usefull proteases may be the trypsin-like proteases, such as trypsin of bovine or porcine origin and proteases from *Fusarium*. In one embodiment of the invention, the detergent composition comprises the polypeptide having endo-beta-1,6-galactanase activity as claimed herein.

In one embodiment of the invention, the detergent adjunct ingredient is selected from the group consisting of surfactants, builders, flocculating aid, chelating agents, dye transfer inhibitors, enzymes, enzyme stabilizers, enzyme inhinitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

The detergent adjunct ingredient may be a surfactant. One advantage of including a surfactant in a detergent composition comprising a polypeptide having endo-beta-1,6-galactanase activity is that the wash performance is improved. The surfactant may be selected among nonionic, anionic and/or amphoteric surfactants as described above, preferably anionic or nonionic surfactants but also amphoteric surfactants may be used. In general, bleach-stable surfactants are preferred, surfactants usefull in compositions of the present invention are described below.

The detergent adjunct ingredient may be a builder. In one embodiment the detergent adjunct ingredient is one ore more builders mentioned below.

The detergent adjunct ingredient may be a bleaching system. The bleaching system can be selected from the group consisting of tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), 6-(phthalimido)peroxyhexanoic acid (PAP), NaHCO$_3$ and/or mixtures thereof. In a preferred embodiment the bleaching system may comprise tetraacetylethylenediamine (TAED) and NaHCO$_3$.

In one embodiment of the invention, the bleaching system comprises a bleach catalyst selected from the group consisting of organic catalysts having the following formulae:

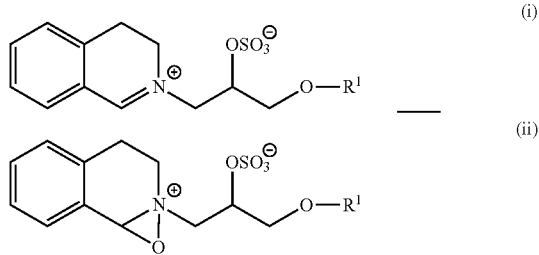

(iii) and mixtures thereof;

wherein each R$^1$ is independently a branched alkyl group containing from 9 to 24 carbons or linear alkyl group containing from 11 to 24 carbons, where each R$^1$ is independently a branched alkyl group containing from 9 to 18 carbons or linear alkyl group containing from 11 to 18 carbons, or where each R$^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl In one embodiment of the invention, detergent adjunct ingredient is an enzyme. The detergent composition may comprise one or more enzymes. The one or more enzymes may be selected from the group consisting of proteases, lipases, cutinases, amylases, carbohydrases, cellulases, pectinases, mannanases, arabinases, galactanases, xylanases and oxidases.

In one embodiment of the invention, the inventive detergent composition is formulated with a protease, which is of animal, vegetable or microbial origin. The protease is chemically modified or protein engineered. The protease can be a serine protease or a metalloprotease, preferably an alkaline microbial protease or a trypsin-like protease.

In one embodiment of the invention, the protease is selected from the group consisting of BPN', subtilisin Novo, subtilisin Carlsberg, subtilisin 309, subtilisin 147, subtilisin 168, *Bacillus lentus* DSM 5483 protease, trypsin-like proteases, proteases from *Fusarium* and variants hereof. In one embodiment the protease is aprotease having at least 50%, such as at least 55%, such as at least 60%, such as at least 65%, such as at least 70%, such as at least 75%, such as at least 80%, such as at least 85%, such as at least 90%, such as at least 95%, sequence identity to SEQ ID NO: 7. In one embodiment the protease has at least 90% identity to the amino acid sequence of SEQ ID NO: 7 or is a variant thereof with a modification such as a substitution in one or more of the following positions corresponding to positions 3, 4, 9, 15, 27, 36, 42, 53, 55, 57, 66, 74, 76, 85, 87, 93, 94, 95, 96, 97, 98, 99, 100, 101, 102, 104, 116, 118, 121, 120, 123, 126, 127, 128, 154, 156, 158, 161, 164, 167, 170, 188, 189, 193, 194, 199, 200, 206, 211, 212, 216, 218, 222, 224, 226, 229, 230, 235, 239, 242, 246, 255, 256 and 268 of SEQ ID NO 7, preferably the variant is an alkaline protease having at least 60%, such as at least 65%, such as at least 70%, such as at least 75%, such as at least 80%, such as at least 85%, such as at least 90%, such as at least 65%, identity to the amino acid sequence of SEQ ID NO: 7 and comprising following modifications: S3T, V4I, S9R,E, A15T, K27R, *36D, N42R, V66A, N74D, N85S,R, A96S, *97E, S97G, D,A, S97AD, S99E,D,G,M,R,N, S101A, V102I,Y,N, S104A, G116V,R, H118D,N, N121S, S126A,L, P127Q, S128A, S154D, S158D, Y161A, R164S, A188P, G189E, V193M, V199I, L211D,Q, N212D, M216S, A226V, K249L, Q230H, Q239R, N246K, N255E,D, L256E,D, T268A, compared to SEQ ID NO 7, which according to conventional BPN' (SEQ ID NO 8) numbering corresponds to S3T, V4I, S9R,E, A15T, K27R, *36D, N43R, V68A, N76D, N87S,R, A98S, *99E, S99G,D,A, S99AD, S101E,D,G,M,R,N, S103A, V104I,Y,N, S106A, G118V,R, H120D,N, N123S, S128A,L, P129Q, S130A, S156D, S160D, Y167A, R170S, A194P, G195E, V199M, V205I, L217D,Q, N218D, M222S, A232V, K255L, Q236H, Q245R, N252K, N261E,D, L262E,D and T274A. The BPN' numbering system is commonly used and is described e.g. in WO 1991/000345 and as shown in FIG. 1 of WO 2004/041979. In one embodiment the protease comprises any of the following substitutions: S9R, S9E, N76D, S99D, S101E, S101D, L217D, S128A, S128L, L217Q, M222S In one embodiment the protease comprises any of the following substitution sets S9R+V66A, V66A+S104A, V66A+N212D, S126A+217Q, S99AD, S9E+N43R, N76D+A194P, S99D+S101E, S101E+V2051 or N76D+G195E.

In one embodiment of the invention, the detergent composition is capable of reducing adhesion of bacteria selected from the group consisting of *Acinetobacter* sp., *Aeromicrobium* sp., *Brevundimonas* sp., *Microbacterium* sp., *Micrococcus luteus*, *Pseudomonas* sp., *Staphylococcus epidermidis*, *Stenotrophomonas* sp. and *Corynebacterium xerosis* to a surface, or releasing the bacteria from a surface to which they adhere.

In one embodiment of the invention, the surface is a textile surface, a dishware surface or a hard surface. The textile can be made of cotton, flax/linen, jute, ramie, sisal, cellulosic textile, viscose/rayon, cellulose acetate (tricill), lyocell, wool, silk, camel, cashmere, mohair, rabbit, nylon, aramid, polyester, acrylic, polypropylene and spandex/elastane, polyamide, polyacryl, or blends thereof as well as blends of cellulose based and non-cellulose based fibers. The detergent composition may be formulated as a bar, a homogenous tablet, a tablet having two or more layers, a pouch having one or more compartments, a regular or compact powder, a granule, a paste, a gel, or a regular, compact or concentrated liquid. The detergent composition can be a liquid detergent, a powder detergent or a granule detergent.

The invention further concerns a method for laundering an item, which method comprises the steps of:
  a. Exposing an item to a wash liquor comprising the polypeptide having endo-beta-1,6-galactanase activity or a detergent composition comprising polypeptide having endo-beta-1,6-galactanase activity;
  b. Completing at least one wash cycle; and c. Optionally rinsing the item,
  wherein the item is a textile, a dishware or a hard surface.

The pH of the wash liquor is in the range of 5.5 to 11, such as in the range of 7 to 9, in the range of 7 to 8 or in the range of 7 to 8.5.

The wash liquor may have a temperature in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C. In one embodiment the temperature of the wash liquor is 30° C.

In one embodiment of the invention, the method for laundering an item further comprises draining of the wash liquor or part of the wash liquor after completion of a wash cycle. The wash liquor can then be re-used in a subsequent wash cycle or in a subsequent rinse cycle. The item may be exposed to the wash liquor during a first and optionally a second or a third wash cycle. In one embodiment, the item is rinsed after being exposed to the wash liquor. The item can be rinsed with water or with water comprising a conditioner.

The invention further concerns an item washed according to the inventive method.

Polypeptides Having Endo-Beta-1,6-Galactanase Activity

A polypeptide having endo-beta-1,6-galactanase activity or a endo-beta-1,6-galactanase is any enzyme that catalyzes the hydrolytic cleavage of 1,6-β-D-galactooligosaccharides with a degree of polymerization (DP) higher than 3, and their acidic derivatives with 4-O-methylglucosyluronate or glucosyluronate groups at the non-reducing terminals. The endo-beta-1,6-galactanase activity can be tested in Assay I as described herein. Thus, a polypeptide having endo-beta-1,6-galactanase activity is a polypeptide that shows activity when tested in Assay I. The two terms polypeptide having endo-beta-1,6-galactanase activity and endo-beta-1,6-galactanase are used interchangeably.

According to the present invention, a endo-beta-1,6-galactanase which is obtainable from a fungus is preferred; in particular a endo-beta-1,6-galactanase which is obtainable from a Trichoderma is preferred; in particular a endo-beta-1,6-galactanase which is obtainable from Trichoderma harzianum is preferred.

The endo-beta-1,6-galactanase used in the present invention includes the mature polypeptide of SEQ ID NO: 2, shown as amino acids 1 to 458 of SEQ ID NO: 2, which is obtained from Trichoderma harzianum.

The endo-beta-1,6-galactanase enzyme may comprise or consist of the amino acid sequence shown as amino acids 1 to 458 of SEQ ID NO: 2 or a fragment thereof that has endo-beta-1,6-galactanase activity, such as the mature polypeptide. Or the endo-beta-1,6-galactanase enzyme may comprise or consist of a fragment of amino acids 11 to 448 of SEQ ID NO: 2 for which fragment one or more amino acids is deleted from the amino and/or carboxyl terminus of SEQ ID NO: 2.

The present invention also provides endo-beta-1,6-galactanase polypeptides that are substantially homologous to the polypeptides above, and species homologs (paralogs or orthologs) thereof. The term "substantially homologous" is used herein to denote polypeptides being at least 80%, preferably at least 85%, more preferably at least 90%, more preferably at least 95%, even more preferably at least 97% identical, and most preferably at least 99% or more identical to the amino acid sequence of SEQ ID NO: 2, or a fragment thereof that has endo-beta-1,6-galactanase activity, or its orthologs or paralogs.

In an embodiment, the present invention relates to polypeptides having a sequence identity to the mature polypeptide of SEQ ID NO: 2 of at least 60% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 65% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 70% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 75% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 80% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 85% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 90% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 91% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 92% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 93% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 94% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 95% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 96% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 97% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 98% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 99% which have endo-beta-1,6-galactanase activity and the polypeptide is used for preventing, reducing or removing a biofilm from an item.

In an embodiment, the present invention relates to polypeptides having a sequence identity to the mature polypeptide of SEQ ID NO: 2 of at least 100% which have endo-beta-1,6-galactanase activity and the polypeptide is used for preventing, reducing or removing a biofilm from an item.

The concentration of the endo-beta-1,6-galactanase in the wash liquor is typically in the range of 0.02-15 ppm enzyme protein, in the range of 0.05-15 ppm enzyme protein, in the range of 0.1-10 ppm enzyme protein, in the range of 0.2-5 ppm enzyme protein, in the range of 0.25-5 ppm enzyme protein, in the range of 0.3-3 ppm enzyme protein, in the range of 0.4-2 ppm enzyme protein or in the range of 0.5-1 ppm enzyme protein.

The endo-beta-1,6-galactanase of the present invention may be added to a detergent composition in an amount corresponding to at least 0.01 mg of endo-beta-1,6-galactanase protein per gram detergent composition, such as at least 0.015 mg of protein, at least 0.1 mg of protein, at least 0.2 mg of protein, at least 0.3 mg of protein, at least 0.5 mg of protein, at least 1 mg of protein or at least 2 mg or protein. Thus, the detergent composition may comprise at least 0.001% endo-beta-1,6-galactanase protein, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of endo-beta-1,6-galactanase protein.

When used in a wash liquor in combination with a protease, the concentration of the endo-beta-1,6-galactanase can be lower than when used alone. The concentration of the endo-beta-1,6-galactanase can be in the range of 0.0025-15 ppm enzyme protein, in the range of 0.005-15 ppm enzyme protein, in the range of 0.01-10 ppm enzyme protein, in the range of 0.02-5 ppm enzyme protein, in the range of 0.025-5 ppm enzyme protein, in the range of 0.025-3 ppm enzyme protein, in the range of 0.025-2 ppm enzyme protein or in the range of 0.025-1 ppm enzyme protein. The concentration of the protease can be in the range of 0.05-100.0 ppm enzyme protein, in the range of 0.05-50.0 ppm enzyme protein, in the range of 0.5-50.0 ppm enzyme protein, in the range of 1.0-20.0 ppm enzyme protein, in the range of 2.0-20.0 ppm enzyme protein, in the range of 2.4-10.0 ppm enzyme protein, in the range of 1.0-5.0 ppm enzyme protein or in the range of 1.0-3.0 ppm enzyme protein.

When used in a detergent composition in combination with a protease, the concentration of the endo-beta-1,6-galactanase can be lower than when used alone. The endo-beta-1,6-galactanase of the present invention may be added to a detergent composition in an amount corresponding to at least 0.01 mg of endo-beta-1,6-galactanase protein per gram detergent composition, such as at least 0.015 mg of protein, at least 0.1 mg of protein, at least 0.2 mg of protein, at least 0.3 mg of protein, at least 0.5 mg of protein, at least 1 mg of protein or at least 2 mg or protein. Thus, the detergent composition may comprise at least 0.00004% endo-beta-1,6-galactanase protein when 0.0048% of the protease of SEQ ID NO: 7 or a protease having at least 60% sequence identity hereto is present. Thus, the detergent composition may comprise at least 0.0001% endo-beta-1,6-galactanase protein when 0.012% of the protease of SEQ ID NO: 7 or a protease having at least 60% sequence identity hereto is present. The detergent composition may comprise at least 0.0004% endo-beta-1,6-galactanase protein when 0.12%% of the protease of SEQ ID NO: 7 or a protease having at least 60% sequence identity hereto is present. The detergent composition may comprise at least 0.0001% endo-beta-1,6-galactanase protein when 0.12% of the protease of SEQ ID NO: 7 or a protease having at least 60% sequence identity hereto is present, preferably at least 0.0002%, 0.0003%, 0.0004%, 0.0005%, 0.0006%, 0.0008%, 0.001%, 0.002%, 0.003%, 0.005%, 0.01%, 0.02%, 0.03%, 0.04%, 0.06%, 0.07%, 0.08%, 0.09%, 0.1%, 0.2%, 0.3%, 0.5%, 0.8%, 1.0%, 1.1 of endo-beta-1,6-galactanase protein.

The detergent composition may comprise granules, which granules comprise a core and a protective coating. The coating may be a coating as described in WO2011/134809. If the enzyme of the composition is used in a liquid detergent composition, the composition may be stabilized with the compound described in WO 2009/118375.

The endo-beta-1,6-galactanase of the detergent composition of the invention may be stabilized using conventional stabilizing agents, e.g. a polyol such as propylene glycol or glycerol, a sugar or sugar alcohol, lactic acid, boric acid, or a boric acid derivative, e.g. an aromatic borate ester, or a phenyl boronic acid derivative such as 4-formylphenyl boronic acid, and the composition may be formulated as described in, for example, WO92/19709 and WO92/19708.

A polypeptide of the present invention may also be incorporated in the detergent formulations disclosed in WO97/07202, which is hereby incorporated by reference.

In an embodiment, the present invention relates to polypeptides having a sequence identity to the mature polypeptide of SEQ ID NO: 2 at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have endo-beta-1,6-galactanase activity. In one aspect, the polypeptides differ by up to 10 amino acids, e.g., 1, 2, 3, 4, 5, 6, 7, 8, 9, or 10, from the mature polypeptide of SEQ ID NO: 2.

In a particular embodiment, the invention relates to polypeptides having a sequence identity to the mature polypeptide of SEQ ID NO: 2 of at least 80%, and wherein the polypeptide has at least at least 70% of the endo-beta-1,6-galactanase activity of the mature polypeptide of SEQ ID NO: 2.

In a particular embodiment, the invention relates to polypeptides having a sequence identity to the mature polypeptide of SEQ ID NO: 2 of at least 85% and wherein the polypeptide has at least at least 75% of the endo-beta-1,6-galactanase activity of the mature polypeptide of SEQ ID NO: 2.

In a particular embodiment, the invention relates to polypeptides having a sequence identity to the mature polypeptide of SEQ ID NO: 2 of at least 90% and wherein the polypeptide has at least at least 80% of the endo-beta-1,6-galactanase activity of the mature polypeptide of SEQ ID NO: 2.

In a particular embodiment, the invention relates to polypeptides having a sequence identity to the mature polypeptide of SEQ ID NO: 2 of at least 91% and wherein the polypeptide has at least at least 85% of the endo-beta-1,6-galactanase activity of the mature polypeptide of SEQ ID NO: 2.

In a particular embodiment, the invention relates to polypeptides having a sequence identity to the mature polypeptide of SEQ ID NO: 2 of at least 92% and wherein the polypeptide has at least 90% of the endo-beta-1,6-galactanase activity of the mature polypeptide of SEQ ID NO: 2.

In a particular embodiment, the invention relates to polypeptides having a sequence identity to the mature polypeptide of SEQ ID NO: 2 of at least 93% and wherein the polypeptide has at least 95% of the endo-beta-1,6-galactanase activity of the mature polypeptide of SEQ ID NO: 2.

In a particular embodiment, the invention relates to polypeptides having a sequence identity to the mature polypeptide of SEQ ID NO: 2 of at least 94% and wherein the polypeptide has at least 100% of the endo-beta-1,6-galactanase activity of the mature polypeptide of SEQ ID NO: 2.

In a particular embodiment, the invention relates to polypeptides having a sequence identity to the mature polypeptide of SEQ ID NO: 2 of at least 95% and wherein the polypeptide has at least 100% of the endo-beta-1,6-galactanase activity of the mature polypeptide of SEQ ID NO: 2.

In a particular embodiment, the invention relates to polypeptides having a sequence identity to the mature polypeptide of SEQ ID NO: 2 of at least 96% and wherein the polypeptide has at least 100% of the endo-beta-1,6-galactanase activity of the mature polypeptide of SEQ ID NO: 2.

In a particular embodiment, the invention relates to polypeptides having a sequence identity to the mature polypeptide of SEQ ID NO: 2 of at least 97% and wherein the polypeptide has at least 100% of the endo-beta-1,6-galactanase activity of the mature polypeptide of SEQ ID NO: 2.

In a particular embodiment, the invention relates to polypeptides having a sequence identity to the mature polypeptide of SEQ ID NO: 2 of at least 98% and wherein the polypeptide has at least 100% of the endo-beta-1,6-galactanase activity of the mature polypeptide of SEQ ID NO: 2.

In a particular embodiment, the invention relates to polypeptides having a sequence identity to the mature polypeptide of SEQ ID NO: 2 of at least 99% and wherein the polypeptide has at least 100% of the endo-beta-1,6-galactanase activity of the mature polypeptide of SEQ ID NO: 2.

In a particular embodiment, the invention relates to polypeptides having a sequence identity to the mature polypeptide of SEQ ID NO: 2 of 100% and wherein the polypeptide has at least 100% of the endo-beta-1,6-galactanase activity of the mature polypeptide of SEQ ID NO: 2.

In an embodiment, the polypeptide has been isolated. A polypeptide of the present invention preferably comprises or consists of the amino acid sequence of SEQ ID NO: 2 or an allelic variant thereof; or is a fragment thereof having endo-beta-1,6-galactanase activity. In another aspect, the polypeptide comprises or consists of the mature polypeptide of SEQ ID NO: 2. In another aspect, the polypeptide comprises or consists of amino acids 1 to 485 of SEQ ID NO: 2. In another embodiment, the present invention relates to a polypeptide having endo-beta-1,6-galactanase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, or (ii) the full-length complement of (i) (Sambrook et al., 1989, Molecular Cloning, A Laboratory Manual, 2d edition, Cold Spring Harbor, N.Y.). In an embodiment, the polypeptide has been isolated.

The polynucleotide of SEQ ID NO: 1 or a subsequence thereof, as well as the polypeptide of SEQ ID NO: 2 or a fragment thereof may be used to design nucleic acid probes to identify and clone DNA encoding polypeptides having endo-beta-1,6-galactanase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a polypeptide having endo-beta-1,6-galactanase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1 (ii) the mature polypeptide coding sequence of SEQ ID NO: 1; (iii) the full-length complement thereof; or (iv) a subsequence thereof; under very low, low stringency conditions, low-medium stringency conditions, medium stringency conditions, medium-high stringency conditions, high stringency conditions or very high stringency conditions. Molecules to which the nucleic acid probe hybridizes under these conditions can be detected using, for example, X-ray film or any other detection means known in the art.

In one aspect, the nucleic acid probe is consists of probe fragments generated from DNA of SEQ ID NO: 1 or subfragments thereof. In another aspect, the nucleic acid probe is a polynucleotide that encodes the polypeptide of SEQ ID NO: 2; the mature polypeptide thereof; or a fragment thereof. In another embodiment, the present invention relates to an polypeptide having endo-beta-1,6-galactanase activity encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant molecules are tested for endo-beta-1,6-galactanase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64.

The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, EMBO J. 12: 2575-2583; Dawson et al., 1994, Science 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, J. Ind. Microbiol. Biotechnol. 3: 568-576; Svetina et al., 2000, J. Biotechnol. 76: 245-251; Rasmussen-Wilson et al., 1997, Appl. Environ. Microbiol. 63: 3488-3493; Ward et al., 1995, Biotechnology 13: 498-503; and Contreras et al., 1991, Biotechnology 9: 378-381; Eaton et al., 1986, Biochemistry 25: 505-512; Collins-Racie et al., 1995, Biotechnology 13: 982-987; Carter et al., 1989, Proteins: Structure, Function, and Genetics 6: 240-248; and Stevens, 2003, Drug Discovery World 4: 35-48.

Sources of Polypeptides Having Endo-Beta-1,6-Galactanase Activity

A polypeptide having endo-beta-1,6-galactanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In another aspect, the polypeptide is a *Trichoderma* polypeptide, e.g., a polypeptide obtained from *Trichorderma harzianum*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide, as described herein. In an embodiment, the polynucleotide encoding the polypeptide of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Trichoderma*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1 e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* crylllA gene (Agaisse and Lereclus, 1994, Molecular Microbiology 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide.

The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells. The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide having endo-beta-1,6-galactanase activity of the present invention, comprising (a) cultivating a cell, which in its wild-type form produces the polypeptide, under conditions conducive for production of the polypeptide; and optionally, (b) recovering the polypeptide. In one aspect, the cell is a *Trichoderma* cell. In another aspect, the cell is a *Trichoderma harzianum* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide having endo-beta-1,6-galactanase activity may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Detergent Compositions

In one embodiment, the invention is directed to detergent compositions comprising a polypeptide having endo-beta-1,6-galactanase activity of the present invention in combination with one or more additional cleaning composition components. The choice of additional components is within the skill of the artisan and includes conventional ingredients, including the exemplary non-limiting components set forth below.

In one embodiment, the invention is directed to an ADW (Automatic Dish Wash) composition comprising an enzyme of the present invention in combination with one or more additional ADW composition components. In one embodiment, the invention is directed to an industrial cleaning composition comprising an enzyme of the present invention in combination with one or more additional industrial cleaning composition components.

In one embodiment, the invention is directed to a laundry powder composition comprising an enzyme of the present invention in combination with one or more additional laundry powder composition components.

In one embodiment, the invention is directed to a liquid detergent composition comprising an enzyme of the present invention in combination with one or more additional liquid detergent composition components. The choice of additional components is within the skill of the artisan and includes conventional ingredients, including the exemplary non-limiting components set forth below.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0% to about 40% by weight of a zwitterionic surfactant. Non-limiting examples of zwitterionic surfactants include betaines such as alkyldimethylbetaines, sulfobetaines, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta (methylenephosphonic acid) (DTPMP), aminotris (methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain 0-30% by weight, such as about 1% to about 20%, of a bleaching system. Any bleaching system known in the art for use in detergents may be utilized. Suitable bleaching system components include bleaching catalysts, photobleaches, bleach activators, sources of hydrogen peroxide such as sodium percarbonate, sodium perborates and hydrogen peroxide-urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone®, and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A particular family of bleach activators of interest was disclosed in EP624154 and particulary preferred in that family is acetyl triethyl citrate (ATC). ATC or a short chain triglyceride like triacetin has the advantage that it is environmentally friendly Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido) peroxyhexanoic acid (PAP).

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2"-nitrilotris(ethane-1,2-diylazanylylidene-κN-methanylylidene)triphenolato-κ3O]manganese(III). The bleach catalysts may also be other metal compounds, such as iron or cobalt complexes.

In some embodiments, the bleach component may be an organic catalyst selected from the group consisting of organic catalysts having the following formulae:

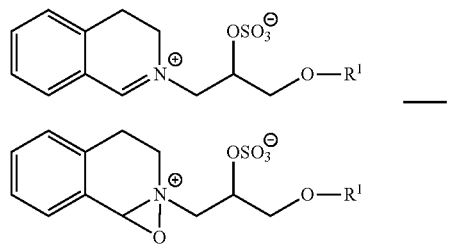

(iii) and mixtures thereof;
wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described,
e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst. The source of peracid may be selected from (a) preformed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO 2007/087243.

Enzymes

The detergent additive as well as the detergent composition may comprise one or more additional enzymes such as a protease, lipase, cutinase, an amylase, carbohydrase, cellulase, pectinase, mannanase, arabinase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO 99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Proteases:

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those obtained from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO 09/021867, and subtilisin lentus, subtilisin Novo, subtilisin Carlsberg, *Bacillus licheniformis*, subtilisin BPN', subtilisin 309, subtilisin 147 and subtilisin 168 described in WO 89/06279 and protease PD138 described in (WO 93/18140). Other useful proteases may be those described in WO 92/175177, WO 01/016285, WO 02/026024 and WO 02/016547. Examples of trypsin-like proteases are trypsin (e.g. of porcine or bovine origin) and the *Fusarium* protease described in WO 89/06270, WO 94/25583 and WO 05/040372, and the chymotrypsin proteases obtained from *Cellumonas* described in WO 05/052161 and WO 05/052146.

A further preferred protease is the alkaline protease from *Bacillus lentus* DSM 5483, as described for example in WO 95/23221, and variants thereof which are described in WO 92/21760, WO 95/23221, EP 1921147 and EP 1921148.

Examples of metalloproteases are the neutral metalloprotease as described in WO 07/044993 (Genencor Int.) such as those obtained from *Bacillus amyloliquefaciens*.

Examples of useful proteases are the variants described in: WO 92/19729, WO 96/034946, WO 98/20115, WO 98/20116, WO 99/011768, WO 01/44452, WO 03/006602, WO 04/03186, WO 04/041979, WO 07/006305, WO 11/036263, WO 11/036264, especially the variants with an alteration in one or more of the following positions corresponding to the positions 3, 4, 9, 15, 27, 36, 42, 53, 55, 57, 66, 74, 76, 85, 87, 93, 94, 95, 96, 97, 98, 99, 100, 101, 102, 104, 116, 118, 121, 120, 123, 126, 127, 128, 154, 156, 158, 161, 164, 167, 170, 188, 189, 193, 194, 199, 200, 206, 211, 212, 216, 218, 222, 224, 226, 229, 230, 235, 239, 242, 246, 255, 256 and 268 of SEQ ID NO 7, preferably the protease variant is an alkaline protease having at least 60%, such as at least 65%, such as at least 70%, such as at least 75%, such as at least 80%, such as at least 85%, such as at least 90%, such as at least 65%, identity to the amino acid sequence of SEQ ID NO: 7 and comprising the following modifications: S3T, V4I, S9R,E, A15T, K27R, *36D, N42R, V66A, N74D, N85S,R, A96S, *97E, S97G,D,A, S97AD, S99E,D,G,M,R, N, S101A, V102I,Y,N, S104A, G116V,R, H118D,N, N121S, S126A,L, P127Q, S128A, S154D, S158D, Y161A, R164S, A188P, G189E, V193M, V199I, L211D,Q, N212D, M216S, A226V, K249L, Q230H, Q239R, N246K, N255E,D, L256E, D, T268A, compared to SEQ ID NO 7. Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase®, Blaze®, (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, FN2®, FN3®, FN4®, Excellase®, Eraser®, Ultimase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases:

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases:

Suitable amylases which can be used together with the polypeptide of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase obtained from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T491+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T 182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one or more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™ Purastar™/Effectenz™, Powerase, Preferenz S1000, Preferenz S100 and Preferenz S110 (from Genencor International Inc./DuPont).

Peroxidases/Oxidases:

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment obtained therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP 179,486), and variants thereof as those described in WO 93/24618, WO 95/10602, and WO 98/15257.

A peroxidase according to the invention also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as *Caldariomyces*, e.g., *C. fumago*, *Alternaria*, *Curvularia*, e.g., *C. verruculosa* and *C. inaequalis*, *Drechslera*, *Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In an preferred embodiment, the haloperoxidase is derivable from *Curvularia* sp., in particular *Curvularia verruculosa* or *Curvularia inaequalis*, such as *C. inaequalis* CBS 102.42 as described in WO 95/27046; or *C. verruculosa* CBS 147.63 or *C. verruculosa* CBS 444.70 as described in WO 97/04102; or from *Drechslera hartlebii* as described in WO 01/79459, *Dendryphiella salina* as described in WO 01/79458, *Phaeotrichoconis crotalarie* as described in WO 01/79461, or *Geniculosporium* sp. as described in WO 01/79460.

An oxidase according to the invention include, in particular, any laccase enzyme comprised by the enzyme classification EC 1.10.3.2, or any fragment obtained therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be obtained from plants, bacteria or fungi (including filamentous fungi and yeasts).

Suitable examples from fungi include a laccase derivable from a strain of *Aspergillus*, *Neurospora*, e.g., *N. crassa*, *Podospora*, *Botrytis*, *Collybia*, *Fomes*, *Lentinus*, *Pleurotus*, *Trametes*, e.g., *T. villosa* and *T. versicolor*, *Rhizoctonia*, e.g., *R. solani*, *Coprinopsis*, e.g., *C. cinerea*, *C. comatus*, *C. friesii*, and *C. plicatilis*, *Psathyrella*, e.g., *P. condelleana*, *Panaeolus*, e.g., *P. papilionaceus*, *Myceliophthora*, e.g., *M. thermophila*, *Schytalidium*, e.g., *S. thermophilum*, *Polyporus*, e.g., *P. pinsitus*, *Phlebia*, e.g., *P. radiata* (WO 92/01046), or *Coriolus*, e.g., *C. hirsutus* (JP 2238885).

Suitable examples from bacteria include a laccase derivable from a strain of *Bacillus*.

A laccase obtained from *Coprinopsis* or *Myceliophthora* is preferred; in particular a laccase obtained from *Coprinopsis cinerea*, as disclosed in WO 97/08325; or from *Myceliophthora thermophila*, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Other Materials

Any detergent components known in the art for use in detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Dispersants

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume.

Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Liquid Detergent Composition

The liquid detergent composition may comprise a microcapsules of the invention, and thus form part of, any detergent composition in any form, such as liquid and powder detergents, and soap and detergent bars.

In one embodiment, the invention is directed to liquid detergent compositions comprising a microcapsule, as described above, in combination with one or more additional cleaning composition components.

The microcapsule, as described above, may be added to the liquid detergent composition in an amount corresponding to from 0.0001% to 5% (w/w) active enzyme protein (AEP); preferably from 0.001% to 5%, more preferably from 0.005% to 5%, more preferably from 0.005% to 4%, more preferably from 0.005% to 3%, more preferably from 0.005% to 2%, even more preferably from 0.01% to 2%, and most preferably from 0.01% to 1% (w/w) active enzyme protein.

The liquid detergent composition has a physical form, which is not solid (or gas). It may be a pourable liquid, a paste, a pourable gel or a non-pourable gel. It may be either isotropic or structured, preferably isotropic. It may be a formulation useful for washing in automatic washing machines or for hand washing. It may also be a personal care product, such as a shampoo, toothpaste, or a hand soap.

The liquid detergent composition may be aqueous, typically containing at least 20% by weight and up to 95% water, such as up to 70% water, up to 50% water, up to 40% water, up to 30% water, or up to 20% water. Other types of liquids, including without limitation, alkanols, amines, diols, ethers and polyols may be included in an aqueous liquid detergent. An aqueous liquid detergent may contain from 0-30% organic solvent. A liquid detergent may even be non-aqueous, wherein the water content is below 10%, preferably below 5%.

Detergent ingredients can be separated physically from each other by compartments in water dissolvable pouches. Thereby negative storage interaction between components can be avoided. Different dissolution profiles of each of the compartments can also give rise to delayed dissolution of selected components in the wash solution.

The detergent composition may take the form of a unit dose product. A unit dose product is the packaging of a single dose in a non-reusable container. It is increasingly used in detergents for laundry. A detergent unit dose product is the packaging (e.g., in a pouch made from a water soluble film) of the amount of detergent used for a single wash.

Pouches can be of any form, shape and material which is suitable for holding the composition, e.g., without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be a blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticizers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids (see e.g., US 2009/0011970).

The choice of detergent components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

Laundry Soap Bars

The polypeptide of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, Polypeptide, optionally one or more additional enzymes, a protease inhibitor, and a salt of a monovalent cation and an organic anion may be prepared and the mixture is then plodded. The Polypeptide and optional additional enzymes may be added at the same time as the protease inhibitor for example in liquid form. Besides the mixing step and the plodding step, the process may further comprise the steps of milling, extruding, cutting, stamping, cooling and/or wrapping.

The invention is further summarized in the following paragraphs:
1. Use of a polypeptide having endo-beta-1,6-galactanase activity for preventing, reducing or removing a biofilm from an item, wherein the item is a textile, a dishware or a hard surface.
2. Use according to paragraph 1 for preventing, reducing or removing stickiness of the item.
3. Use according to any of paragraphs 1 or 2 for pretreating biofilm present on the item.
4. Use according to any of paragraphs 1-3 for preventing, reducing or removing redeposition of soil during a wash cycle.
5. Use according to any of paragraphs 1-4 for preventing, reducing or removing adherence of soil to the item.
6. Use according to any of the preceding paragraphs for maintaining or improving whiteness of the item.
7. Use according to any of the preceding paragraphs, wherein the whiteness is further improved by the combined use of the polypeptide having endo-beta-1,6-galactanase activity and a bleaching system.
8. Use according to paragraph 7, wherein the bleaching system is selected from the group consisting of tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), 6-(phthalimido) peroxyhexanoic acid (PAP), $NaHCO_3$ and/or mixtures thereof.
9. Use according to paragraph 7, wherein the bleaching system comprises a bleach catalyst selected from the group consisting of organic catalysts having the following formulae:

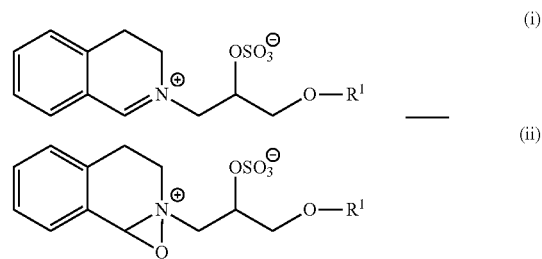

(iii) and mixtures thereof;
wherein each $R^1$ is independently a branched alkyl group containing from 9 to 24 carbons or linear alkyl group containing from 11 to 24 carbons, where each $R^1$ is independently a branched alkyl group containing from 9 to 18 carbons or linear alkyl group containing from 11 to 18 carbons, or where each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.
10. Use according to any of the preceding paragraphs, wherein the polypeptide having endo-beta-1,6-galactanase activity is used together with a protease.
11. Use according to paragraph 10, wherein the protease boosts the polypeptide having endo-beta-1,6-galactanase activity.
12. Use according to any of the preceding paragraphs, wherein the polypeptide having endo-beta-1,6-galactanase is obtained from fungal source.
13. Use according to paragraph 12, wherein the polypeptide is obtained from *Trichoderma*.
14. Use according to any of paragraphs 12-13, wherein the polypeptide is obtained from *Trichoderma harzianum*.
15. Use according to any of paragraphs 12-14, wherein the polypeptide is a polypeptide having endo-beta-1,6-galactanase activity, selected from the group consisting of:
   (a) a polypeptide having at least 60% sequence identity to the mature polypeptide of SEQ ID NO: 2;
   (b) a polypeptide encoded by a polynucleotide that hybridizes under medium stringency conditions with (i) the mature polypeptide coding sequence of SEQ ID NO: 1, or (ii) the full-length complement of (i);
   (c) a polypeptide encoded by a polynucleotide having at least 60% sequence identity to the mature polypeptide coding sequence of SEQ ID NO: 1;
   (d) a variant of the mature polypeptide of SEQ ID NO: 2 comprising a substitution, deletion, and/or insertion at one or more positions; and (e) a fragment of the polypeptide of (a), (b), (c), or (d) that has endo-beta-1,6-galactanase activity.
16. A detergent composition comprising a polypeptide having endo-beta-1,6-galactanase activity and a detergent adjunct ingredient.
17. Detergent composition according to paragraph 12, wherein the polypeptide is obtained from *Trichoderma*.
18. Detergent composition according to any of the preceding composition paragraphs, wherein the polypeptide is obtained from *Trichoderma harzianum*.
19. Detergent composition according to any of the preceding paragraphs, wherein the polypeptide is the polypeptide of paragraphs 59-66.
20. Detergent composition according to any of the preceding composition paragraphs, wherein the detergent adjunct ingredient is selected from the group consisting of surfactants, builders, flocculating aid, chelating agents, dye transfer inhibitors, enzymes, enzyme stabilizers, enzyme inhinitors, catalytic materials, bleaching system, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.
21. Detergent composition according to any of the preceding composition paragraphs, wherein the detergent adjunct ingredient is a surfactant.
22. Detergent composition according to any of the preceding composition paragraphs, wherein the detergent adjunct ingredient is a builder.
23. Detergent composition according to any of the preceding composition paragraphs, wherein the bleaching system is selected from the group consisting of tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), 6-(phthalimido)peroxyhexanoic acid (PAP), NaHCO$_3$ and/or mixtures thereof.
24. Detergent composition according to paragraphs 23, wherein the bleaching system comprises tetraacetylethylenediamine (TAED) and NaHCO$_3$.
25. Detergent composition according to any of the preceding composition paragraphs, wherein the bleaching system comprises a bleach catalyst selected from the group consisting of organic catalysts having the following formulae:

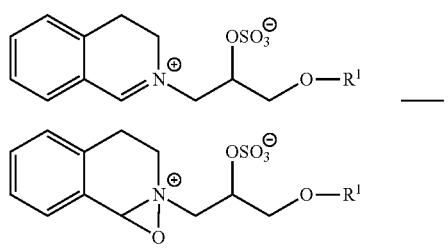

(iii) and mixtures thereof;
wherein each R$^1$ is independently a branched alkyl group containing from 9 to 24 carbons or linear alkyl group containing from 11 to 24 carbons, where each R$^1$ is independently a branched alkyl group containing from 9 to 18 carbons or linear alkyl group containing from 11 to 18 carbons, or where each R$^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl 26. Detergent composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases, peroxydases and oxidases.
27. Detergent composition according to any of the preceding composition paragraphs, wherein the enzyme is a protease, which is of animal, vegetable or microbial origin.
28. Detergent composition according to any of the preceding composition paragraphs, wherein the protease is chemically modified or protein engineered.
29. Detergent composition according to any of the preceding composition paragraphs, wherein the protease is a serine protease or a metalloprotease, preferably an alkaline microbial protease or a trypsin-like protease.
30. Detergent composition according to any of the preceding composition paragraphs, wherein the protease is selected from the group consisting of BPN', subtilisin Novo, subtilisin Carlsberg, subtilisin 309, subtilisin 147, subtilisin 168, *Bacillus lentus* DSM 5483 protease, trypsin-like proteases, proteases from *Fusarium* and variants hereof.
31. Detergent composition according to any of the preceding composition paragraphs, wherein the protease has at least 60%, such as at least 70%, such as at least 75%, such as at least 80%, such as at least 85%, such as at least 90%, such as at least 95% sequence identity to SEQ ID NO: 7.
32. Detergent composition according to any of the preceding paragraphs, wherein the protease has at least 90% identity to the amino acid sequence of SEQ ID NO: 7 or a variant thereof with substitutions in one or more of the following positions corresponding to the positions: 3, 4, 9, 15, 27, 36, 42, 53, 55, 57, 66, 74, 76, 85, 87, 93, 94, 95, 96, 97, 98, 99, 100, 101, 102, 104, 116, 118, 121, 120, 123, 126, 127, 128, 154, 156, 158, 161, 164, 167, 170, 188, 189, 193, 194, 199, 200, 206, 211, 212, 216, 218, 222, 224, 226, 229, 230, 235, 239, 242, 246, 255, 256 and 268 of SEQ ID NO 7, preferably the variant is an alkaline protease having at least 90% identity to the amino acid sequence of SEQ ID NO: 7 with the following substitution: S9R, S9E, N76D, S99D, S101E, S101D, L217D, S128A, S128L, L217Q, M222S or substitutions N76D+G195E (using BPN' numbering).
33. Detergent composition according to any of the preceding composition paragraphs, wherein the detergent composition is capable of reducing adhesion of bacteria selected from the group consisting of *Acinetobacter* sp., *Aeromicrobium* sp., *Brevundimonas* sp., *Microbacterium* sp., *Micrococcus luteus*, *Pseudomonas* sp., *Staphylococcus epidermidis*, and *Stenotrophomonas* sp., *Corynebacterium xerosis* to a surface, or releasing the bacteria from a surface to which they adhere.
34. Detergent composition according to any of the preceding composition paragraphs, wherein the surface is a textile surface, a dishware surface or a hard surface.
35. Detergent composition according to paragraph 34, wherein the textile is made of cotton, flax/linen, jute, ramie, sisal, cellulosic textile, viscose/rayon, cellulose acetate (tricill), lyocell, wool, silk, camel, cashmere, mohair, rabbit, nylon, aramid, polyester, acrylic, polypropylene and spandex/elastane, polyamide, polyacryl, or blends thereof as well as blends of cellulose based and non-cellulose based fibers 36. Detergent composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid.

37. Detergent composition according to any of the preceding composition paragraphs, wherein the composition is a liquid detergent, a powder detergent or a granule detergent.

38. A washing method for washing an item comprising the steps of:
   a. Exposing the item to a wash liquor comprising a polypeptide of paragraphs 61-68 or a detergent composition according to any of paragraphs 16-37;
   b. Completing at least one wash cycle; and
   c. Optionally rinsing the item,
   wherein the item is a textile, a dishware or a hard surface.

39. Method according to paragraph 38, wherein the pH of the wash liquor is in the range of 5.5 to 11.

40. Method according to any of the preceding method paragraphs, wherein the pH of the wash liquor is in the range of 7 to 9, in the range of 7 to 8 or in the range of 7.5 to. 8.5

41. Method according to any of the preceding method paragraphs, wherein the temperature of the wash liquor is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C.

42. Method according to any of the preceding method paragraphs, wherein the temperature of the wash liquor is 30° C.

43. Method according to any of the preceding method paragraphs, wherein the method further comprises draining of the wash liquor or part of the wash liquor after completion of a wash cycle.

44. Method according to any of the preceding method paragraphs, wherein the item is exposed to the wash liquor during a first and optionally a second or a third wash cycle.

45. Method according to any of the preceding method paragraphs, wherein the item is rinsed after being exposed to the wash liquor.

46. Method according to any of the preceding method paragraphs, wherein the item is rinsed with water or with water comprising a conditioner.

47. Method according to any of the preceding method paragraphs, wherein stickiness of the item is reduced.

48. Method according to any of the preceding method paragraphs, wherein stains present on the item is pretreated with a polypeptide of paragraphs 47-56 or a detergent composition according to any of paragraphs 16-34.

49. Method according to any of the preceding method paragraphs, wherein redeposition of soil is prevented or reduced.

50. Method according to any of the preceding method paragraphs, wherein adherence of soil to the item is prevented, reduced or removed.

51. Method according to any of the preceding method paragraphs, wherein whiteness of the item is maintained or improved.

52. Method according to paragraph 51, wherein the whiteness is further improved by the combined use of the polypeptide having endo-beta-1,6-galactanase activity and a bleaching system.

53. Method according to paragraph 52, wherein the bleaching system is selected from the group consisting of tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), 6-(phthalimido)peroxyhexanoic acid (PAP), $NaHCO_3$ and/or mixtures thereof.

54. Method according to paragraph 52-53, wherein the bleaching system comprises tetraacetylethylenediamine (TAED) and $NaHCO_3$.

55. Method according to any of paragraphs 52-54, wherein the bleaching system comprises a bleach catalyst selected from the group consisting of organic catalysts having the following formulae:

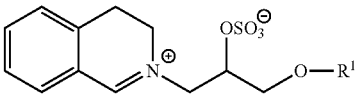

(i)

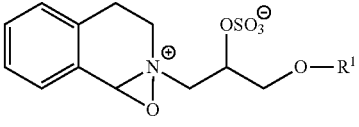

(ii)

(iii) and mixtures thereof;
wherein each $R^1$ is independently a branched alkyl group containing from 9 to 24 carbons or linear alkyl group containing from 11 to 24 carbons, where each $R^1$ is independently a branched alkyl group containing from 9 to 18 carbons or linear alkyl group containing from 11 to 18 carbons, or where each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

56. Method according to any of the preceding method paragraphs, wherein the item is a textile.

57. Method according to any of the preceding method paragraphs, wherein the item is a dishware.

58. Method according to any of the preceding method paragraphs, wherein the item is a hard surface.

59. Method according to any of the preceding method paragraphs, wherein the concentration of the polypeptide in the wash liquor is in the range of typically in the range of 0.02-15 ppm enzyme protein, in the range of 0.05-15 ppm enzyme protein, in the range of 0.1-10 ppm enzyme protein, in the range of 0.2-5 ppm enzyme protein, in the range of 0.25-5 ppm enzyme protein, in the range of 0.3-3 ppm enzyme protein, in the range of 0.4-2 ppm enzyme protein or in the range of 0.5-1 ppm enzyme protein.

60. Method according to any of the preceding method paragraphs, wherein the concentration of the protease is in the range of 0.05-100.0 ppm enzyme protein, in the range of 0.05-50.0 ppm enzyme protein, in the range of 0.5-50.0 ppm enzyme protein, in the range of 1.0-20.0 ppm enzyme protein, in the range of 2.0-20.0 ppm enzyme protein, in the range of 2.4-10.0 ppm enzyme protein, in the range of 1.0-5.0 ppm enzyme protein or in the range of 1.0-3.0 ppm enzyme protein.

61. A polypeptide having endo-beta-1,6-galactanase activity, selected from the group consisting of:
    (a) a polypeptide having at least 60% sequence identity to the mature polypeptide of SEQ ID NO: 2;
    (b) a polypeptide encoded by a polynucleotide that hybridizes under medium stringency conditions with (i) the mature polypeptide coding sequence of SEQ ID NO: 1, or (ii) the full-length complement of (i);
    (c) a polypeptide encoded by a polynucleotide having at least 60% sequence identity to the mature polypeptide coding sequence of SEQ ID NO: 1;
    (d) a variant of the mature polypeptide of SEQ ID NO: 2 comprising a substitution, deletion, and/or insertion at one or more positions; and
    (e) a fragment of the polypeptide of (a), (b), (c), or (d) that has endo-beta-1,6-galactanase activity.
62. The polypeptide of paragraph 61, having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2.
63. The polypeptide of paragraph 61 or 62, which is encoded by a polynucleotide that hybridizes under low stringency conditions, low-medium stringency conditions, medium stringency conditions, medium-high stringency conditions, high stringency conditions, or very high stringency conditions with (i) the mature polypeptide coding sequence of SEQ ID NO: 1, or (ii) the full-length complement of (i).
64. The polypeptide of any of paragraphs 61-63, which is encoded by a polynucleotide having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1.
65. The polypeptide of any of paragraphs 61-64, comprising or consisting of SEQ ID NO: 2 or the mature polypeptide of SEQ ID NO: 2.
66. The polypeptide of paragraph 65, wherein the mature polypeptide is amino acids 1 to 458 of SEQ ID NO: 2.
67. The polypeptide of any of paragraphs 61-66, which is a variant of the mature polypeptide of SEQ ID NO: 2 comprising a substitution, deletion, and/or insertion at one or more positions.
68. The polypeptide of paragraph 67, which is a fragment of SEQ ID NO: 2, wherein the fragment has endo-beta-1,6-galactanase activity.
69. A polynucleotide encoding the polypeptide of any of paragraphs 61-68.
70. A nucleic acid construct or expression vector comprising the polynucleotide of paragraph 69 operably linked to one or more control sequences that direct the production of the polypeptide in an expression host.
71. A recombinant host cell comprising the polynucleotide of paragraph 70 operably linked to one or more control sequences that direct the production of the polypeptide.
72. A method of producing the polypeptide of any of paragraphs 61-68, comprising cultivating a cell, which in its wild-type form produces the polypeptide, under conditions conducive for production of the polypeptide.
73. The method of paragraph 72, further comprising recovering the polypeptide.
74. A method of producing a polypeptide having endo-beta-1,6-galactanase activity, comprising cultivating the host cell of paragraph 71 under conditions conducive for production of the polypeptide.
75. The method of paragraph 74, further comprising recovering the polypeptide.
76. A whole broth formulation or cell culture composition comprising a polypeptide of any of paragraphs 61-68.

Assays and Detergent Compositions
Detergent Compositions
Composition of Ariel Sensitive White & Color, Liquid Detergent Composition:

Aqua, Alcohol Ethoxy Sulfate, Alcohol Ethoxylate, Amino Oxide, Citrid Acid, C12-18 topped palm kernel fatty acid, Protease, Glycosidase, Amylase, Ethanol, 1,2 Propanediol, Sodium Formate, Calcium Chloride, Sodium hydroxide, Silicone Emulsion, Trans-sulphated EHDQ (the ingredients are listed in descending order).

Composition of WFK IEC-A Model Detergent (Powder)

Ingredients: Linear sodium alkyl benzene sulfonate 8.8%, Ethoxylated fatty alcohol C12-18 (7 EO) 4.7%, Sodium soap 3.2%, Anti foam DC2-4248S 3.9%, Sodium aluminium silicate zeolite 4A 28.3%, Sodium carbonate 11.6%, Sodium salt of a copolymer from acrylic and maleic acid (Sokalan CP5) 2.4%, Sodium silicate 3.0%, Carboxymethylcellulose 1.2%, Dequest 2066 2.8%, Optical whitener 0.2%, Sodium sulfate 6.5%, Protease 0.4%.

Composition of Model Detergent a (Liquid)

Ingredients: 12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w)

Composition of Ariel Actilift (Liquid)

Ingredients: 5-15% Anionic surfactants; <5% Non-ionic surfactants, Phosphonates, Soap; Enzymes, Optical brighteners, Benzisothiazolinone, Methylisothiazolinone, Perfumes, Alpha-isomethyl ionone, Citronellol, Geraniol, Linalool.

Composition of Ariel Actilift Colour & Style

Aqua, Sodium Dodecylbenzenesulfonate, C14-C15 Pareth-7, Sodium Citrate, Propylene Glycol, Sodium Palm Kernelate, Sodium Laureth Sulfate, MEA Dodecylbenzenesulfonage, Sulfated Ethoxylated Hexamethylenediamine Quaternized, Sodium Cumenesulfonate, Perfume, Co-polymer of PEG/Vinyl Acetate, Sodium formate, Hydrogenated Castor Oil, Sodium Diethylenetriamine Pentamethylene Phosphonate, PEG/PPG-10/2 Propylheptyl Ether, Butyophenyl Methylpropional, Polyvinylpyridine-N-Oxide, Sorbitol, Glycerin, Ethanolamine, Sodium Hydroxide, Alpha-Isomethyl Ionone, Protease, Calcium Chloride, Geraniol, Linalool, Citronelllol, Tripropylene Glycol, Glycosidase, Benzisothiazolinone, Dimethicone, Glycosidase, Sodium Acetate, Cellulase, Colorant, Glyceryl Stearate, Hydroxyethylcellulose, Silica.

Composition of Ariel Actilift Colour & Style, New Pack

Ingredients: Aqua, Sodium Laureth Sulfate, Propylene Glycol, C14-C15 Pareth-7, Sodium citrate, Sodium Palm Kernelate, Alcohol, Sodium Formate, Sulfated Ethoxylated Hexamethylenediamine Quaternized, Sodium Hydroxide, Perfume, Polyvinylpyridine-N-Oxide, Sorbitol, Calcium Chloride, protease, Glycerin, Glucosidase, Glycosidase, Sodium Acetate, Colorant, Cellulase.

Composition of Ariel Actilift Whites & Colours Coolclean, New Pack

Ingredients: Aqua, Sodium Laureth Sulfate, Propylene Glycol, C14-C15 Pareth-7, Sodium citrate, Sodium Palm Kernelate, Alcohol, Sodium Formate, Sulfated Ethoxylated Hexamethylenediamine Quaternized, Sodium Hydroxide, Perfume, Sorbitol, Calcium Chloride, protease, Glycerin, Glucosidase, Glycosidase, Sodium Acetate, Colorant, Cellulase.

Composition of Ariel Sensitive White & Color

Ingredients: Aqua, Sodium Laureth Sulfate, Propylene Glycol, C14-C15 Pareth-7, Sodium citrate, Sodium Palm Kernelate, Alcohol, Sodium Formate, Sulfated Ethoxylated Hexamethylenediamine Quaternized, Sodium Hydroxide, Sorbitol, Calcium Chloride, protease, Glycerin, Glycosidase, Sodium Acetate, Cellulase, Silica.

Composition of Ariel Actilift, Regular

Aqua, Sodium Dodecylbenzenesulfonate, C14-C15 Pareth-7, Sodium Citrate, Propylene Glycol, Sodium Palm Kernelate, Sodium Laureth Sulfate, MEA Dodecylbenzenesulfonage, Sulfated Ethoxylated Hexamethylenediamine Quaternized, Sodium Cumenesulfonate, Perfume, Co-polymer of PEG/Vinyl Acetate, Sodium formate, C12-C14 Pareth-7, Hydrogenated Castor Oil, Sodium Diethylenetriamine Pentamethylene Phosphonate, PEG/PPG-10/2 Propylheptyl Ether, Butyophenyl Methylpropional, Fluorescent Brightener 9, Sorbitol, Glycerin, Ethanolamine, Sodium Hydroxide, Alpha-Isomethyl Ionone, Protease, Calcium Chloride, Geraniol, Linalool, Citronelllol, Tripropylene Glycol, Sodium Chloride, Glycosidase, Benzisothiazolinone, Dimethicone, Glycosidase, Sodium Acetate, Cellulase, Colorant, Glyceryl Stearate, Hydroxyethylcellulose, Silica.

Composition of Persil Small & Mighty (Liquid)

Ingredients: 15-30% Anionic surfactants, Non-ionic surfacts, 5-15% Soap, <5% Polycarboxylates, Perfume, Phosphates, Optical Brighteners Composition of Fairy Non Bio (Liquid)

Ingredients: 15-30% Anionic Surfactants, 5-15% Non-Ionic Surfactants, Soap, Benzisothiazolinone, Methylisothiazolinone, Perfumes Composition of Model Detergent T (Powder)

Ingredients: 11% LAS, 2% AS/AEOS, 2% soap, 3% AEO, 15.15% sodium carbonate, 3% sodium silcate, 18.75% zeolite, 0.15% chelant, 2% sodium citrate, 1.65% AA/MA copolymer, 2.5% CMC and 0.5% SRP (all percentages are w/w).

Composition of Model Detergent X (Powder)

Ingredients: 16.5% LAS, 15% zeolite, 12% sodium disilicate, 20% sodium carbonate, 1% sokalan, 35.5% sodium sulfate (all percentages are w/w).

Composition of Ariel Actilift (Powder)

Ingredients: 15-30% Anionic surfactants, <5% Non-ionic surfactants, Phosphonates, Polycarboxylates, Zeolites; Enzymes, Perfumes, Hexyl cinnamal.

Composition of Persil Megaperls (Powder)

Ingredients: 15-30% of the following: anionic surfactants, oxygen-based bleaching agent and zeolites, less than 5% of the following: non-ionic surfactants, phosphonates, polycarboxylates, soap, Further ingredients: Perfumes, Hexyl cinnamal, Benzyl salicylate, Linalool, optical brighteners, Enzymes and Citronellol.

Gain Liquid, Original:

Ingredients: Water, Alcohol Ethoxysulfate, Diethylene Glycol, Alcohol Ethoxylate, Ethanolamine, Linear Alkyl Benzene Sulfonate, Sodium Fatty Acids, Polyethyleneimine Ethoxylate, Citric Acid, Borax, Sodium Cumene Sulfonate, Propylene Glycol, DTPA, Disodium Diaminostilbene Disulfonate, Dipropylethyl Tetramine, Sodium Hydroxide, Sodium Formate, Calcium Formate, Dimethicone, Amylase, Protease, Liquitint™, Hydrogenated Castor Oil, Fragrance Tide Liquid, Original:

Ingredients: Linear alkylbenzene sulfonate, propylene glycol, citric acid, sodium hydroxide, borax, ethanolamine, ethanol, alcohol sulfate, polyethyleneimine ethoxylate, sodium fatty acids, diquaternium ethoxysulfate, protease, diethylene glycol, laureth-9, alkyldimethylamine oxide, fragrance, amylase, disodium diaminostilbene disulfonate, DTPA, sodium formate, calcium formate, polyethylene glycol 4000, mannanase, Liquitint™ Blue, dimethicone.

Liquid Tide, Free and Gentle:

Water, sodium alcoholethoxy sulfate, propylene glycol, borax, ethanol, linear alkylbenzene sulfonate sodium, salt, polyethyleneimine ethoxylate, diethylene glycol, trans sulfated & ethoxylated hexamethylene diamine, alcohol ethoxylate, linear alkylbenzene sulfonate, MEA salt, sodium formate, sodium alkyl sulfate, DTPA, amine oxide, calcium formate, disodium diaminostilbene, disulfonate, amylase, protease, dimethicone, benzisothiazolinone Tide Coldwater Liquid, Fresh Scent:

Water, alcoholethoxy sulfate, linear alkylbenzene sulfonate, diethylene glycol, propylene glycol, ethanolamine, citric acid, Borax, alcohol sulfate, sodium hydroxide, polyethyleneimine, ethoxylate, sodium fatty acids, ethanol, protease, Laureth-9, diquaternium ethoxysulfate, lauramine oxide, sodium cumene, sulfonate, fragrance, DTPA, amylase, disodium, diaminostilbene, disulfonate, sodium formate, disodium distyrylbiphenyl disulfonate, calcium formate, polyethylene glycol 4000, mannanase, pectinase, Liquitint™ Blue, dimethicone Tide TOTALCARE™ Liquid, Cool Cotton:

Water, alcoholethoxy sulfate, propylene glycol, sodium fatty acids, laurtrimonium chloride, ethanol, sodium hydroxide, sodium cumene sulfonate, citric acid, ethanolamine, diethylene glycol, silicone polyether, borax, fragrance, polyethyleneimine ethoxylate, protease, Laureth-9, DTPA, polyacrylamide quaternium chloride, disodium diaminostilbene disulfonate, sodium formate, Liquitint™ Orange, dipropylethyl tetraamine, dimethicone, cellulase, Liquid Tide Plus Bleach Alternative™, Vivid White and Bright, Original and Clean Breeze:

Water, sodium alcoholethoxy sulfate, sodium alkyl sulfate, MEA citrate, linear alkylbenzene sulfonate, MEA salt, propylene glycol, diethylene glycol, polyethyleneimine ethoxylate, ethanol, sodium fatty acids, ethanolamine, lauramine oxide, borax, Laureth-9, DTPA, sodium cumene sulfonate, sodium formate, calcium formate, linear alkylbenzene sulfonate, sodium salt, alcohol sulfate, sodium hydroxide, diquaternium ethoxysulfate, fragrance, amylase, protease, mannanase, pectinase, disodium diaminostilbene disulfonate, benzisothiazolinone, Liquitint™ Blue, dimethicone, dipropylethyl tetraamine.

Liquid Tide HE, Original Scent:

Water, Sodium alcoholethoxy sulfate, MEA citrate, Sodium Alkyl Sulfate, alcohol ethoxylate, linear alkylbenzene sulfonate, MEA salt, sodium fatty acids, polyethyleneimine ethoxylate, diethylene glycol, propylene glycol, diquaternium ethoxysulfate, borax, polyethyleneimine, ethoxylate propoxylate, ethanol, sodium cumene sulfonate, fragrance, DTPA, disodium diaminostilbene disulfonate, Mannanase, cellulase, amylase, sodium formate, calcium formate, Lauramine oxide, Liquitint™ Blue, Dimethicone/polydimethyl silicone.

Tide TOTALCARE HE Liquid, Renewing Rain:

Water, alcoholethoxy sulfate, linear alkylbenzene sulfonate, alcohol ethoxylate, citric acid, Ethanolamine, sodium fatty acids, diethylene glycol, propylene glycol, sodium hydroxide, borax, polyethyleneimine ethoxylate, silicone polyether, ethanol, protease, sodium cumene sulfonate, diquaternium ethoxysulfate, Laureth-9, fragrance, amylase, DTPA, disodium diaminostilbene disulfonate, disodium distyrylbiphenyl disulfonate, sodium formate, calcium formate, mannanase, Liquitint™ Orange, dimethicone, polyacrylamide quaternium chloride, cellulase, dipropylethyl tetraamine.

Tide Liquid HE Free:

Water, alcoholethoxy sulfate, diethylene glycol, monoethanolamine citrate, sodium formate, propylene glycol, linear alkylbenzene sulfonates, ethanolamine, ethanol, polyethyleneimine ethoxylate, amylase, benzisothiazolin, borax, calcium formate, citric acid, diethylenetriamine pentaacetate sodium, dimethicone, diquaternium ethoxysulfate, disodium diaminostilbene disulfonate, Laureth-9, mannanase, protease, sodium cumene sulfonate, sodium fatty acids.

Tide Coldwater HE Liquid, Fresh Scent:

Water, alcoholethoxy sulfate, MEA Citrate, alcohol sulfate, Alcohol ethoxylate, Linear alkylbenzene sulfonate MEA, sodium fatty acids, polyethyleneimine ethoxylate, diethylene glycol, propylene glycol, diquaternium ethoxysulfate, borax, polyethyleneimine ethoxylate propoxylate, ethanol, sodium cumene sulfonate, fragrance, DTPA, disodium diaminostilbene disulfonate, protease, mannanase, cellulase, amylase, sodium formate, calcium formate, lauramine oxide, Liquitint™ Blue, dimethicone.

Tide for Coldwater HE Free Liquid:

Water, sodium alcoholethoxy sulfate, MEA Citrate, Linear alkylbenzene sulfonate: sodium salt, Alcohol ethoxylate, Linear alkylbenzene sulfonate: MEA salt, sodium fatty acids, polyethyleneimine ethoxylate, diethylene glycol, propylene glycol, diquaternium ethoxysulfate, Borax, protease, polyethyleneimine ethoxylate propoxylate, ethanol, sodium cumene sulfonate, Amylase, citric acid, DTPA, disodium diaminostilbene disulfonate, sodium formate, calcium formate, dimethicone.

Tide Simply Clean & Fresh:

Water, alcohol ethoxylate sulfate, linear alkylbenzene sulfonate Sodium/Mea salts, propylene glycol, diethylene glycol, sodium formate, ethanol, borax, sodium fatty acids, fragrance, lauramine oxide, DTPA, Polyethylene amine ethoxylate, calcium formate, disodium diaminostilbene disulfonate, dimethicone, tetramine, Liquitint™ Blue.

Tide Pods, Ocean Mist, Mystic Forest, Spring Meadow:

Linear alkylbenzene sulfonates, C12-16 Pareth-9, propylene glycol, alcoholethoxy sulfate, water, polyethyleneimine ethoxylate, glycerine, fatty acid salts, PEG-136 polyvinyl acetate, ethylene Diamine disuccinic salt, monoethanolamine citrate, sodium bisulfite, diethylenetriamine pentaacetate sodium, disodium distyrylbiphenyl disulfonate, calcium formate, mannanase, exyloglucanase, sodium formate, hydrogenated castor oil, natalase, dyes, termamyl, subtilisin, benzisothiazolin, perfume.

Tide to Go:

Deionized water, Dipropylene Glycol Butyl Ether, Sodium Alkyl Sulfate, Hydrogen Peroxide, Ethanol, Magnesium Sulfate, Alkyl Dimethyl Amine Oxide, Citric Acid, Sodium Hydroxide, Trimethoxy Benzoic Acid, Fragrance.

Tide Stain Release Liquid:

Water, Alkyl Ethoxylate, Linear Alkylbenzenesulfonate, Hydrogen Peroxide, Diquaternium Ethoxysulfate, Ethanolamine, Disodium Distyrylbiphenyl Disulfonate, tetrabutyl Ethylidinebisphenol, F&DC Yellow 3, Fragrance.

Tide Stain Release Powder:

Sodium percarbonate, sodium sulfate, sodium carbonate, sodium aluminosilicate, nonanoyloxy benzene sulfonate, sodium polyacrylate, water, sodium alkylbenzenesulfonate, DTPA, polyethylene glycol, sodium palmitate, amylase, protease, modified starch, FD&C Blue 1, fragrance.

Tide Stain Release, Pre Treater Spray:

Water, Alkyl Ethoxylate, MEA Borate, Linear Alkylbenzenesulfonate, Propylene Glycol, Diquaternium Ethoxysulfate, Calcium Chlorideenzyme, Protease, Ethanolamine, Benzoisothiazolinone, Amylase, Sodium Citrate, Sodium Hydroxide, Fragrance.

Tide to Go Stain Eraser: Water, Alkyl Amine Oxide, Dipropylene Glycol Phenyl Ether, Hydrogen Peroxide, Citric Acid, Ethylene Diamine Disuccinic Acid Sodium salt, Sodium Alkyl Sulfate, Fragrance.

Tide Boost with Oxi:

Sodium bicarbonate, sodium carbonate, sodium percarbonate, alcohol ethoxylate, sodium chloride, maleic/acrylic copolymer, nonanoyloxy benzene sulfonate, sodium sulfate, colorant, diethylenetriamine pentaacetate sodium salt, hydrated aluminosilicate (zeolite), polyethylene glycol, sodium alkylbenzene sulfonate, sodium palmitate, starch, water, fragrance.

Tide Stain Release Boost Duo Pac:

Polyvinyl Alcoholpouch film, wherein there is packed a liquid part and a powder part:

Liquid Ingredients:

Dipropylene Glycol, diquaternium Ethoxysulfate, Water, Glycerin, Liquitint™ Orange, Powder Ingredients: sodium percarbonate, nonanoyloxy benzene sulfonate, sodium carbonate, sodium sulfate, sodium aluminosilicate, sodium polyacrylate, sodium alkylbenzenesulfonate, maleic/acrylic copolymer, water, amylase, polyethylene glycol, sodium palmitate, modified starch, protease, glycerine, DTPA, fragrance.

Tide Ultra Stain Release:

Water, sodium alcoholethoxy sulfate, linear alkyl benzene sulfonate, sodium/MEA salts, MEA citrate, propylene glycol, polyethyleneimine ethoxylate, ethanol, diethylene glycol, polyethyleneimine propoxyethoxylate, sodium fatty acids, protease, borax, sodium cumene sulfonate, DTPA, fragrance, amylase, disodium diaminostilbene disulfonate, calcium formate, sodium formate, gluconase, dimethicone, Liquitint™ Blue, mannanase.

Ultra Tide with a Touch of Downy® Powdered Detergent, April Fresh/Clean Breeze/April Essence:

Sodium Carbonate, Sodium Aluminosilicate, Sodium Sulfate, Linear Alkylbenzene Sulfonate, Bentonite, Water, Sodium Percarbonate, Sodium Polyacrylate, Silicate, Alkyl Sulfate, Nonanoyloxybenzenesulfonate, DTPA, Polyethylene Glycol 4000, Silicone, Ethoxylate, fragrance, Polyethylene Oxide, Palmitic Acid, Disodium Diaminostilbene Disulfonate, Protease, Liquitint™ Red, FD&C Blue 1, Cellulase.

Ultra Tide with a Touch of Downy Clean Breeze:

Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimine, propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, sodium formate, Liquitint™ Blue.

Ultra Tide with Downy Sun Blossom:

Water, sodium alcoholethoxy sulfate, MEA citrate, linear alkyl benzene sulfonate: sodium/MEA salts, propylene glycol, ethanol, diethylene glycol, polyethyleneimine propoxyethoxylate, polyethyleneimine ethoxylate, alcohol sulfate, dimethicone, fragrance, borax, sodium fatty acids, DTPA, protease, sodium bisulfite, disodium diaminostilbene disulfonate, amylase, castor oil, calcium formate, MEA, styrene acrylate copolymer, propanaminium propanamide, gluconase, sodium formate, Liquitint™ Blue.

Ultra Tide with Downy April Fresh/Sweet Dreams:

Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimin propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, propanaminium propanamide, sodium formate, Liquitint™ Blue.

Ultra Tide Free Powdered Detergent:

Sodium Carbonate, Sodium Aluminosilicate, Alkyl Sulfate, Sodium Sulfate, Linear Alkylbenzene Sulfonate, Water, Sodium polyacrylate, Silicate, Ethoxylate, Sodium percarbonate, Polyethylene Glycol 4000, Protease, Disodium Diaminostilbene Disulfonate, Silicone, Cellulase.

Ultra Tide Powdered Detergent, Clean Breeze/Spring Lavender/Mountain Spring:

Sodium Carbonate, Sodium Aluminosilicate, Sodium Sulfate, Linear Alkylbenzene Sulfonate, Alkyl Sulfate, Sodium Percarbonate, Water, Sodium Polyacrylate, Silicate, Nonanoyloxybenzenesulfonate, Ethoxylate, Polyethylene Glycol 4000, Fragrance, DTPA, Disodium Diaminostilbene Disulfonate, Palmitic Acid, Protease, Silicone, Cellulase.

Ultra Tide HE (High Efficiency) Powdered Detergent, Clean Breeze:

Sodium Carbonate, Sodium Aluminosilicate, Sodium Sulfate, Linear Alkylbenzene Sulfonate, Water, Nonanoyloxybenzenesulfonate, Alkyl Sulfate, Sodium Polyacrylate, Silicate, Sodium Percarbonate, Ethoxylate, Polyethylene Glycol 4000, Fragrance, DTPA, Palmitic Acid, Disodium Diaminostilbene Disulfonate, Protease, Silicone, Cellulase.

Ultra Tide Coldwater Powdered Detergent, Fresh Scent:

Sodium Carbonate, Sodium Aluminosilicate, Sodium Sulfate, Sodium Percarbonate, Alkyl Sulfate, Linear Alkylbenzene Sulfonate, Water, Nonanoyloxybenzenesulfonate, Sodium Polyacrylate, Silicate, Ethoxylate, Polyethylene Glycol 4000, DTPA, Fragrance, Natalase, Palmitic Acid, Protease, Disodium, Diaminostilbene Disulfonate, FD&C Blue 1, Silicone, Cellulase, Alkyl Ether Sulfate.

Ultra Tide with Bleach Powdered Detergent, Clean Breeze:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate, Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

Ultra Tide with Febreeze Freshness™ Powdered Detergent, Spring Renewal:

Sodium Carbonate, Sodium Aluminosilicate, Sodium Sulfate, Linear Alkylbenzene Sulfonate, Sodium Percarbonate, Alkyl Sulfate, Water, Sodium Polyacrylate, Silicate, Nonanoyloxybenzenesulfonate, Ethoxylate, Polyethylene Glycol 4000, DTPA, Fragrance, Cellulase, Protease, Disodium Diaminostilbene Disulfonate, Silicone, FD&C Blue 1.

Liquid Tide Plus with Febreeze Freshness—Sport HE Active Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, Ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Plus Febreeze Freshness Spring & Renewal:

Water, sodium alcoholethoxy sulfate, linear alkyl benzene sulfonate: sodium/MEA salts, MEA citrate, propylene glycol, polyethyleneimine ethoxylate, fragrance, ethanol, diethylene glycol, polyethyleneimine propoxyethoxylate, protease, alcohol sulfate, borax, sodium fatty acids, DTPA, disodium diaminostilbene disulfonate, MEA, mannanase, gluconase, sodium formate, dimethicone, Liquitint™ Blue, tetramine.

Liquid Tide Plus with Febreeze Freshness, Sport HE Victory Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Vivid White+Bright Powder, Original:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

| Ingredient | Amount (in wt %) |
| --- | --- |
| Anionic detersive surfactant (such as alkyl benzene sulphonate, alkyl ethoxylated sulphate and mixtures thereof) | from 8 wt % to 15 wt % |
| Non-ionic detersive surfactant (such as alkyl ethoxylated alcohol) | from 0.5 wt % to 4 wt % |
| Cationic detersive surfactant (such as quaternary ammonium compounds) | from 0 to 4 wt % |
| Other detersive surfactant (such as zwiterionic detersive surfactants, amphoteric surfactants and mixtures thereof) | from 0 wt % to 4 wt % |
| Carboxylate polymer (such as co-polymers of maleic acid and acrylic acid) | from 1 wt % to 4 wt % |
| Polyethylene glycol polymer (such as a polyethylene glycol polymer comprising poly vinyl acetate side chains) | from 0.5 wt % to 4 wt % |
| Polyester soil release polymer (such as Repel-o-tex from and/or Texcare polymers) | 0.1 to 2 wt % |
| Cellulosic polymer (such as carboxymethyl cellulose, methyl cellulose and combinations thereof) | from 0.5 wt % to 2 wt % |
| Other polymer (such as amine polymers, dye transfer inhibitor polymers, | from 0 wt % to 4 wt % |

| Ingredient | Amount |
|---|---|
| hexamethylenediamine derivative polymers, and mixtures thereof) | |
| Zeolite builder and phosphate builder (such as zeolite 4A and/or sodium tripolyphosphate) | from 0 wt % to 4 wt % |
| Other builder (such as sodium citrate and/or citric acid) | from 0 wt % to 3 wt % |
| Carbonate salt (such as sodium carbonate and/or sodium bicarbonate) | from 15 wt % to 30 wt % |
| Silicate salt (such as sodium silicate) | from 0 wt % to 10 wt % |
| Filler (such as sodium sulphate and/or bio-fillers) | from 10 wt % to 40 wt % |
| Source of available oxygen (such as sodium percarbonate) | from 10 wt % to 20 wt % |
| Bleach activator (such as tetraacetylethylene diamine (TAED) and/or nonanoyloxybenzenesulphonate (NOBS) | from 2 wt % to 8 wt % |
| Bleach catalyst (such as oxaziridinium-based bleach catalyst and/or transition metal bleach catalyst) | from 0 wt % to 0.1 wt % |
| Other bleach (such as reducing bleach and/or pre- formed peracid) | from 0 wt % to 10 wt % |
| Chelant (such as ethylenediamine-N'N'-disuccinic acid (EDDS) and/or hydroxyethane diphosphonic acid(HEDP) | from 0.2 wt % to1 wt % |
| Photobleach (such as zinc and/or aluminium sulphonated phthalocyanine) | from 0 wt % to 0.1 wt % |
| Hueing agent (such as direct violet 99, acid red 52, acid blue 80, direct violet 9, solvent violet 13 and any combination thereof) | from 0 wt % to 1 wt % |
| Brightener (such as brightener 15 and/or brightener 49) | from 0.1 wt % to 0.4 wt % |
| Protease (such as Savinase, Savinase Ultra, Purafect, FN3, FN4 and any combination thereof) | from 0.1 wt % to 0.4 wt % |
| Amylase (such as Termamyl, Termamyl ultra Natalase, Optisize, Stainzyme, Stainzyme Plus, and any combination thereof) | from 0.05 wt % to 0.2 wt % |
| Cellulase (such as Carezyme and/or Celluclean) | from 0.05 wt % to 0.2 wt % |
| Lipase (such as Lipex, Lipolex, Lipoclean and any combination thereof) | from 0.2 to 1 wt % |
| Other enzyme (such as xyloglucanase, cutinase, pectate lyase, mannanase, bleaching enzyme) | from 0 wt % to 2 wt % |
| Fabric softener (such as montmorillonite clay and/or polydimethylsiloxane (PDMS) | from 0 wt % to 4 wt % |
| Flocculant (such as polyethylene oxide) | from 0 wt % to 1 wt % |
| Suds suppressor (such as silicone and/or fatty acid) | from 0 wt % to 0.1 wt % |
| Perfume (such as perfume microcapsule, spray-on perfume, starch encapsulated perfume accords, perfume loaded zeolite, and any combination thereof) | from 0.1 wt % to 1 wt % |
| Aesthetics (such as coloured soap rings and/or coloured speckles/noodles) | from 0 wt % to 1 wt % |
| Miscellaneous | balance |

| Ingredient | Amount |
|---|---|
| Carboxyl group-containing polymer (comprising from about 60% to about 70% by mass of an acrylic acid-based monomer (A); and from about 30% to about 40%) by mass of a sulfonic acid group-containing monomer (B); and wherein the average molecular weight is from about 23,000 to about 50,000 preferably in the range of from about 25,000 to about 38,000 as described in WO2014032269. | from about 0.5 wt % to about 1.5 wt % |
| Amylase (Stainzyme Plus(R)), having an enzyme activity of 14 mg active enzyme/g) | from about 0.1 wt % to about 0.5 wt % |
| Anionic detersive surfactant (such as alkyl benzene sulphonate, alkyl ethoxylated sulphate and mixtures thereof) | from about 8 wt % to about 15 wt % |
| Non-ionic detersive surfactant (such as alkyl ethoxylated alcohol) | from about 0.5 wt % to 4 wt % |
| Cationic detersive surfactant (such as quaternary ammonium compounds) | from about 0 wt % to about 4 wt % |
| Other detersive surfactant (such as zwiterionic detersive surfactants, amphoteric surfactants and mixtures thereof) | from about 0 wt % to 4 wt % |
| Carboxylate polymer (such as co-polymers of maleic acid and acrylic acid) | from about 1 wt % to about 4 wt % |
| Polyethylene glycol polymer (such as a polyethylene glycol polymer comprising poly vinyl acetate side chains) | from about 0 wt % to about 4 wt % |
| Polyester soil release polymer (such as Repel-O- Tex(R) and/or Texcare(R) polymers) | from about 0.1 wt % to about 2 wt % |
| Cellulosic polymer (such as carboxy-methyl cellulose, methyl cellulose and combinations thereof) | from about 0.5 wt % to about 2 wt % |
| Other polymer (such as amine polymers, dye transfer inhibitor polymers, hexamethylenediamine derivative polymers, and mixtures thereof) | from about 0 wt % to about 4 wt % |
| Zeolite builder and phosphate builder (such as zeolite 4A and/or sodium tripolyphosphate) | from about 0 wt % to about 4 wt % |
| Other builder (such as sodium citrate and/or citric acid) | from about 0 wt % to about 3 wt % |
| Carbonate salt (such as sodium carbonate and/or sodium bicarbonate) | from about 15 t % to about 30 wt % |
| Silicate salt (such as sodium silicate) | from about 0 wt % to about 10 wt % |
| Filler (such as sodium sulphate and/or bio-fillers) | from about 10 wt % to about 40 wt % |
| Source of available oxygen (such as sodium percarbonate) | from about 10 wt % to about 20 wt % |
| Bleach activator (such as tetraacetylethylene diamine (TAED) and/or nonanoyloxybenzenesulphonate (NOBS) | from about 2 wt % to about 8 wt % |
| Bleach catalyst (such as oxaziridinium-based bleach catalyst and/or transition metal bleach catalyst) | from about 0 wt % to about 0.1 wt % |
| Other bleach (such as reducing bleach and/or pre formed peracid) | from about 0 wt % to about 10 wt % |
| Chelant (such as ethylenediamine-N'N'-disuccinic acid (EDDS) and/or hydroxyethane diphosphonic acid (HEDP) | from about 0.2 wt % to about 1 wt % |
| Photobleach (such as zinc and/or aluminium sulphonated phthalocyanine) | from about 0 wt % to about 0.1 wt % |
| Hueing agent (such as direct violet 99, acid red 52, acid blue 80, direct violet 9, solvent violet 13 and any combination thereof) | from about 0 wt % to about 0.5 wt % |
| Brightener (such as brightener 15 and/or brightener 49) | from about 0.1 wt % to about 0.4 wt % |
| Protease (such as Savinase, Polarzyme, Purafect, FN3, FN4 and any combination thereof, typically having an enzyme activity of from about 20 mg to about 100 mg active enzyme/g) | from about 0.1 wt % to about 1.5 wt % |
| Amylase (such as Termamyl(R), Termamyl Ultra(R), Natalase(R), Optisize HT Plus(R), Powerase(R), Stainzyme(R) and any combination thereof, typically having an enzyme activity of from about 10 mg to about 50 mg active enzyme/g) | from about 0.05 wt % to about 0.2 wt % |
| Cellulase (such as Carezyme(R), Celluzyme(R) and/or Celluclean(R), typically having an enzyme activity of about from 10 to 50 mg active enzyme/g) | from about 0.05 wt % to 0.5 wt % |
| Lipase (such as Lipex(R), Lipolex(R), Lipoclean(R) and any combination thereof, typically having an enzyme activity of from about 10 mg to about 50 mg active enzyme/g) | from about 0.2 wt % to about 1 wt % |
| Other enzyme (such as xyloglucanase (e.g., Whitezyme(R)), cutinase, pectate lyase, mannanase, bleaching enzyme, typically having an enzyme activity of from about 10 mg to about 50 mg active enzyme/g) | from 0 wt % to 2 wt % |

| | |
|---|---|
| Fabric softener (such as montmorillonite clay and/or polydimethylsiloxane (PDMS)) | from 0 wt % to 15 wt % |
| Flocculant (such as polyethylene oxide) | from 0 wt % to 1 wt % |
| Suds suppressor (such as silicone and/or fatty acid) | from 0 wt % to 0.1 wt % |
| Perfume (such as perfume microcapsule, spray-on perfume, starch encapsulated perfume accords, perfume loaded zeolite, and any combination thereof) | from 0.1 wt % to 1 wt % |
| Aesthetics (such as colored soap rings and/or colored speckles/noodles) | from 0 wt % to 1 wt % |
| Miscellaneous | Balance |

All enzyme levels expressed as rug active enzyme protein per 100 g detergent composition.

Surfactant ingredients can be obtained from BASF, Ludwigshafen, Germany (Lutensol®); Shell Chemicals, London, UK; Stepan, Northfield, Ill., USA; Huntsman, Huntsman, Salt Lake City, Utah, USA; Clariant, Sulzbach, Germany (Praepagen®). Sodium tripolyphosphate can be obtained from Rhodia, Paris, France. Zeolite can be obtained from Industrial Zeolite (UK) Ltd, Grays, Essex, UK. Citric acid and sodium citrate can be obtained from Jungbunzlauer, Basel, Switzerland. NOBS is sodium nonanoyloxybenzenesulfonate, supplied by Eastman, Batesville, Ark., USA.

TAED is tetraacetylethylenediamine, supplied under the Peractive® brand name by Clariant GmbH, Sulzbach, Germany.

Sodium carbonate and sodium bicarbonate can be obtained from Solvay, Brussels, Belgium.

Polyacrylate, polyacrylate/maleate copolymers can be obtained from BASF, Ludwigshafen, Germany.

Repel-O-Tex® can be obtained from Rhodia, Paris, France.

Texcare® can be obtained from Clariant, Sulzbach, Germany. Sodium percarbonate and sodium carbonate can be obtained from Solvay, Houston, Tex., USA.

Na salt of Ethylenediamine-N,N'-disuccinic acid, (S,S) isomer (EDDS) was supplied by Octel, Ellesmere Port, UK.

Hydroxy ethane di phosphonate (HEDP) was supplied by Dow Chemical, Midland, Mich., USA.

Enzymes Savinase®, Savinase® Ultra, Stainzyme® Plus, Lipex®, Lipolex®, Lipoclean®, Celluclean®, Carezyme®, Natalase®, Stainzyme®, Stainzyme® Plus, Termamyl®, Termamyl® ultra, and Mannaway® can be obtained from Novozymes, Bagsvaerd, Denmark.

Enzymes Purafect®, FN3, FN4 and Optisize can be obtained from Genencor International Inc., Palo Alto, Calif., US.

Direct violet 9 and 99 can be obtained from BASF DE, Ludwigshafen, Germany. Solvent violet 13 can be obtained from Ningbo Lixing Chemical Co., Ltd. Ningbo, Zhejiang, China.

Brighteners can be obtained from Ciba Specialty Chemicals, Basel, Switzerland. All percentages and ratios are calculated by weight unless otherwise indicated. All percentages and ratios are calculated based on the total composition unless otherwise indicated. It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Wash Assays

Terg-O-Tometer (TOM) Wash Assay

The Tergo-To-Meter (TOM) is a medium scale model wash system that can be applied to test 12 different wash conditions simultaneously. A TOM is basically a large temperature controlled water bath with up to 12 open metal beakers submerged into it. Each beaker constitutes one small top loader style washing machine and during an experiment, each of them will contain a solution of a specific detergent/enzyme system and the soiled and unsoiled fabrics its performance is tested on. Mechanical stress is achieved by a rotating stirring arm, which stirs the liquid within each beaker. Because the TOM beakers have no lid, it is possible to withdraw samples during a TOM experiment and assay for information on-line during wash.

The TOM model wash system is mainly used in medium scale testing of detergents and enzymes at US or LA/AP wash conditions. In a TOM experiment, factors such as the ballast to soil ratio and the fabric to wash liquor ratio can be varied. Therefore, the TOM provides the link between small scale experiments, such as AMSA and mini-wash, and the more time consuming full scale experiments in top loader washing machines.

Equipment: The water bath with 12 steel beakers and 1 rotating arm per beaker with capacity of 500 or 1200 mL of detergent solution. Temperature ranges from 5 to 80° C. The water bath has to be filled up with deionised water. Rotational speed can be set up to 70 to 120 rpm/min.

Set temperature in the Terg-O-Tometer and start the rotation in the water bath. Wait for the temperature to adjust (tolerance is +/−0.5° C.)

All beakers shall be clean and without traces of prior test material.

Prepare wash solution with desired amount of detergent, temperature and water hardness in a bucket. Let detergent dissolve during magnet stirring for 10 min. Wash solution shall be used within 30 to 60 min after preparation.

Add 600 ml wash solution into a TOM beaker

Start agitation at 120 rpm and optionally add enzymes to the beaker.

Sprinkle the swatches into the beaker and then the ballast load.

Time measurement start when the swatches and ballast are added to the beaker.

Wash for 35 minutes

Stop agitation

Transfer the wash load from TOM beaker to a sieve and rinse with cold tap water

Separate the soil swatches from the ballast load. The soil swatches are transferred to a 5 L beaker with cold tap water under running water. Keep the ballast load separately for the coming inactivation.

Set the timer to 5 minutes.

Press gently the water out by hand and place the test swatches on a tray covered with a paper. Add another paper on top of the swatches.

Let the swatches dry over night and then measure at the Color Eye as described below.

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

In miniLOM, washes are performed in 50 ml test tubes placed in Stuart rotator.

Evaluation of Stains

Wash performance is expressed as a measurement of remission at 460 nm. The higher the remission is, the more light-colored it is and can be used as an assessment of how close it is to white textile. The textile is pre-washed in order to remove finishing products and then it is measured to give a reference value for the clean textile that the experiment swatches can be compared with. Afer washing and rinsing the swatches was spread out and allowed to air dry at room temperature over night. All swatches were avaluated the day after the wash light reflectance evalutations of the swathces was done using a Macbeth color Eye 7000 refelctance spectrophotometer with large aperture. The measurements were made without UV in the incident light and remission 460 nm was extracted.

Enzyme Assays

Assay I: Testing of Galactanase Activity.

Activity Screening of 1,6-Beta Galactanase on Larchwood Arabinogalactan Modified by Acid Hydrolysis 1,6-Galactanase Activity The activity was determined by reducing ends using the colorimetric assay developed by Lever (Analytical Biochemistry 47, 273-279, 1972). The 1,6-beta galactanase was found to produce reducing ends which react with the p-Hydroxybenzoic Acid Hydrazide Solution (PAHBAH, Sigma) generating an increase of colour which is proportional to the enzyme activity under the conditions used in the assay. The table below shows the activity of 1,6-beta galactanase measured by the respective absorbance compared to that of the substrate alone.

Materials and Chemicals:

0.1% Substrate: Larchwood arabino galactan in water MQ.

Activity buffer: 100 mM acetate, 100 mM 2-(N-morpholino)ethanesulfonic acid (MES), 100 mM Glycine in 0.01% Triton (Concentrated stock 100×), 1 mM $CaCl_2$, pH 7.

Ka-Na-tartrate/NaOH: For 1l Ka-Na-tartrate/NaOH solution. Stop solution: Dissolve PAHBAH (Sigma H-9882) in Ka-Na-tartrate/NaOH solution to 15 mg/ml.

Sample Preparation:

The enzyme beta-1,6-galactanase (with protein ID: P34A98 belonging to GH30_5 family) was assay in a final concentration of 60 ppm. Each sample containing substrate only, enzyme only and substrate+enzyme were incubated 1 h at pH 7 and 37 C. After incubation the samples were used for reducing ends, LC-MS and High Performance Anion Exchange Chromatography with Pulsed Amperometric Detection (HPAEC-PAD).

For Reducing Ends as Follows:

50 µl samples were transferred to the PCR-plate.

50 µl activity buffer (pH 8) mix and 50 µl substrate were added and mixed.

Add 75 µl of the Stop solution as described in materials and methods.

The mix was incubated in 10 min. at 95° C., then 1 min. 10° C.

Transfer manually 150 µl to new 96 micro titter plate (MTP), measure absorbance at 405 nm.

For Activity by LC-MS:

LC-MS/PMP Derivatization

LC-MS: The analysis is performed using an LTQ Deca max IonTrap equipped with an Electrospray ionization source (ESI) and an Accela HPLC system with a PDA detector. A BEH Acquity CSH C18 column (2.1×100 mm) is used for the separation at a flow rate of 250 µL/min and 65° C. The gradient is as follows: A: 0.15% HCOOH in water, B: HCOOH in MeCN; 0 min 17% B, 4 min 17% B, 24 min 50% B, 25 min 95% B, 26 min 17% B, 30 min 17% B. 5 µL of samples is injected and UV detection is at 245 nm. The spray settings are as follows: Capillary temp 275° C., sheath gas flow 40 l/min and source voltage of 5 kV.

Phenyl-Methyl Pyrazoline (PMP)-Derivatization:

Add 200 µL sample to a suitable vial (for HPLC)

Add 20 µL 4 M NaOH (ensure that pH>9)

Add 200 µL 0.5 M PMP solution in methanol

Close vial and mix. Incubate at 70° C. for 30 min

Cool to room temperature. Add 20 µL 4 M HCl and mix.

Add 1 ml MQ.

Activity Screening of 1,6-Endo-Beta-Galactanase on Larchwood Arabinogalactan Modified by Acid Hydrolysis 1,6-Galactanase Activity The activity was determined by reducing ends using the colorimetric assay developed by Lever (Analytical Biochemistry 47, 273-279, 1972). The 1,6-beta galactanase was found to produce reducing ends which react with the p-Hydroxybenzoic Acid Hydrazide Solution (PAHBAH, Sigma) generating an increase of colour which is proportional to the enzyme activity under the conditions used in the assay. The table below shows the activity of 1,6-beta galactanase measured by the respective absorbance compared to that of the substrate alone.

Materials and Chemicals:

0.1% Substrate: Larchwood arabino galactan in water MQ.

Activity buffer: 100 mM acetate, 100 mM 2-(N-morpholino)ethanesulfonic acid (MES), 100 mM Glycine in 0.01% Triton (Concentrated stock 100×), 1 mM $CaCl_2$, pH 7.

Ka-Na-tartrate/NaOH: For 1l Ka-Na-tartrate/NaOH solution. Stop solution: Dissolve PAHBAH (Sigma H-9882) in Ka-Na-tartrate/NaOH solution to 15 mg/ml.

Sample Preparation:

The enzyme endo-beta-1,6-galactanase SEQ ID NO: 2 was assay in a final concentration of 60 ppm. Each sample containing substrate only, enzyme only and substrate+enzyme were incubated 1 h at pH 7 and 37 C. After incubation the samples were used for reducing ends, LC-MS and High Performance Anion Exchange Chromatography with Pulsed Amperometric Detection (HPAEC-PAD).

For Reducing Ends as Follows:

50 µl samples were transferred to the PCR-plate.

50 µl activity buffer (pH 8) mix and 50 µl substrate were added and mixed.

Add 75 µl of the Stop solution as described in materials and methods.

The mix was incubated in 10 min. at 95° C., then 1 min. 10° C.

Transfer manually 150 µl to new 96 micro titter plate (MTP), measure absorbance at 405 nm For Activity by LC-MS:

LC-MS/PMP Derivatization

LC-MS: The analysis is performed using an LTQ Deca max IonTrap equipped with an Electrospray ionization source (ESI) and an Accela HPLC system with a PDA detector. A BEH Acquity CSH C18 column (2.1×100 mm) is used for the separation at a flow rate of 250 µL/min and 65° C. The gradient is as follows: A: 0.15% HCOOH in water, B: HCOOH in MeCN; 0 min 17% B, 4 min 17% B, 24 min 50% B, 25 min 95% B, 26 min 17% B, 30 min 17% B. 5 µL of samples is injected and UV detection is at 245 nm. The spray settings are as follows: Capillary temp 275° C., sheath gas flow 40 l/min and source voltage of 5 kV.

Phenyl-Methyl Pyrazoline (PMP)-Derivatization:
  Add 200 µL sample to a suitable vial (for HPLC)
  Add 20 µL 4 M NaOH (ensure that pH>9)
  Add 200 µL 0.5 M PMP solution in methanol
  Close vial and mix. Incubate at 70° C. for 30 min
  Cool to room temperature. Add 20 µL 4 M HCl and mix. Add 1 ml MQ.

For HPAEC-PAD Chromatography:
  The samples were filtered into HPLC vials and run over a gradient as follows: The samples were run on a PA10 column using the following method: Flow 0.8 ml/min

| Time (min) | MQ | NaOH | NaAcO |
| --- | --- | --- | --- |
| 0 | 97 | 3 | 0 |
| 4.5 | 90 | 10 | 0 |
| 23 | 22.4 | 13.6 | 64 |
| 24 | 8 | 12 | 80 |

With all three methods we have confirmed the activity of SEQ ID NO: 2 and it showed to produce Galactose and Galactobiose as main products.

EXAMPLES

Example 1

Cloning of the P34A98 GH30 Polypeptide Coding Sequence from *Trichoderma harzianum* O4.

The P34A98 GH30 polypeptide coding sequence was cloned from *Trichoderma harzianum* O4 DNA by PCR.

*Trichoderma harzianum* O4 was cultivated in 100 ml of YP+2% glucose medium in 1000 ml Erlenmeyer shake flasks for 5 days at 20° C. Mycelia were harvested from the flasks by filtration of the medium through a Buchner vacuum funnel lined with MIRACLOTH® (EMD Millipore, Billerica, Mass., USA). Mycelia were frozen in liquid nitrogen and stored at −80 C until further use. Genomic DNA was isolated using a DNEASY® Plant Maxi Kit (QIAGEN GMBH, Hilden Germany) according to the manufacturer's instructions.

Genomic sequence information was generated by Illumina MySeq (Illumina Inc., San Diego, Calif.). 5 µgs of the isolated *Trichoderma harzianum* genomic DNA was used for library preparation and analysis according to the manufacturers instructions. A 300 bp, paired end strategy was employed with a library insert size of 200-500 bp. One half of a HiSeq run was used for the total of 4,300,311,407 300 bp raw reads obtained. The reads were subsequently fractionated to 25% followed by trimming (extracting longest sub-sequences having Phred-scores of 10 or more). These reads were assembled using Idba version 0.18. Contigs shorter than 200 bp were discarded, resulting in 39,391,155 bp with an N-50 of 167,714. Genes were called using GeneMark.hmm ES version 2.3c and identification of the catalytic domain was made using "GH30" Hidden Markov Model provided by Pfam. The polypeptide coding sequence for the entire coding region was cloned from *Trichoderma harzianum* O4 genomic DNA by PCR using the primers (SEQ ID NO: 3 and SEQ ID NO: 4) described below.

```
                                          (SEQ ID NO: 3)
5'-ACACAACTGGGGATCCACCATGCGATCAGCTATTACTCCATCG-3'

(SEQ ID NO: 4)
5'-AGATCTCGAGAAGCTTATCATTTCAGCACAACACCACT-3'
```

Bold letters represent *Trichoderma harzianum* enzyme coding sequence. Restriction sites are underlined. The sequence to the left of the restriction sites is homologous to the insertion sites of pDau109 (WO 2005/042735).

In-Fusion™ Advantage PCR Cloning Kit Cat. nr 639620

The amplification reaction (50 µl) was performed according to the manufacturer's instructions (Thermo Scientific) with the following final concentrations 1× Phusion HC buffer
200 uM dNTP
2.0 mM MgCl2
0.5 uM of each primer of SEQ ID NO: 3+4.
10 ng of *Trichoderma harzianum* O4 genomic DNA.

The PCR reaction was incubated in a DYAD® Dual-Block Thermal Cycler (BioRad, USA) programmed for 1 cycle at 98° C. for 2 minutes; 30 cycles each at 98° C. for 10 seconds and 72° C. for two minutes followed by 1 cycle at 72° C. for 6 minutes. Samples were cooled to 10° C. before removal and further processing.

Five µl of the PCR reaction were analyzed by 1% agarose gel electrophoresis using 40 mM Tris base, 20 mM sodium acetate, 1 mM disodium EDTA (TAE) buffer. A major band of about 1.4 kb was observed. The remaining PCR reaction was purified directly with an ILLUSTRA™ GFX™ PCR DNA and Gel Band Purification Kit (GE Healthcare, Piscataway, N.J., USA) according to the manufacturer's instructions.

Two µg of plasmid pDau109 was digested with Bam HI and Hind III and the digested plasmid was run on a 1% agarose gel using 50 mM Tris base-50 mM boric acid-1 mM disodium EDTA (TBE) buffer in order to remove the stuffer fragment from the restricted plasmid. The bands were visualized by the addition of SYBR® Safe DNA gel stain (Life Technologies Corporation, Grand Island, N.Y., USA) and use of a 470 nm wavelength transilluminator. The band corresponding to the restricted plasmid was excised and purified using an ILLUSTRA™ GFX™ PCR DNA and Gel Band Purification Kit. The plasmid was eluted into 10 mM Tris pH 8.0 and its concentration adjusted to 20 ng per µl. An IN-FUSION® PCR Cloning Kit (Clontech Laboratories, Inc., Mountain View, Calif., USA) was used to clone the 1450 bp PCR fragment into pDau109 digested with Bam HI and Hind III (20 ng). The IN-FUSION® total reaction volume was 10 µl. The IN-FUSION® total reaction volume was 10 µl. The IN-FUSION® reaction was transformed into FUSION-BLUE™ *E. coli* cells (Clontech Laboratories, Inc., Mountain View, Calif., USA) according to the manufacturer's protocol and plated onto LB agar plates supplemented with 50 µg of ampicillin per ml. After incubation overnight at 37° C., transformant colonies were observed growing under selection on the LB plates supplemented with 50 µg of ampicillin per ml.

Several colonies were selected for analysis by colony PCR using the pDau109 vector primers described below. Four colonies were transferred from the LB plates supplemented with 50 µg of ampicillin per ml with a yellow inoculation pin (Nunc A/S, Denmark) to new LB plates supplemented with 50 µg of ampicillin per ml and incubated overnight at 37° C.

```
                                        (SEQ ID NO: 5)
Primer 8653:    5'-GCAAGGGATGCCATGCTTGG-3'

(SEQ ID NO: 6)
Primer 8654:    5'-CATATAACCAATTGCCCTC-3'
```

Each of the three colonies were transferred directly into 200 µl PCR tubes composed of 5 µl of 2× Thermo Scientific Dream Taq™ PCR Master Mix (Thermo Fisher Scientific, Rockford, Ill., USA), 0.5 µl of primer 8653 (10 pm/µl), 0.5 µl of primer 8654 (10 pm/µl), and 4 µl of deionized water. Each colony PCR was incubated in a DYAD® Dual-Block Thermal Cycler programmed for 1 cycle at 94° C. for 60 seconds; 30 cycles each at 95° C. for 30 seconds, 60° C. for 45 seconds, 72° C. for 60 seconds, 68° C. for 10 minutes, and 10° C. for 10 minutes.

Four µl of each completed PCR reaction were submitted to 1% agarose gel electrophoresis using TAE buffer. All four E. coli transformants showed a PCR band of 1450 bp. Plasmid DNA was isolated from each of the four colonies using a QIAprep Spin Miniprep Kit (QIAGEN GMBH, Hilden Germany). The resulting plasmid DNA was sequenced with primers 8653 and 8654 using an Applied Biosystems Model 3730 Automated DNA Sequencer using version 3.1 BIG-DYE™ terminator chemistry (Applied Biosystems, Inc., Foster City, Calif., USA). One plasmid, designated pKKSC0371-1

Plasmid pKKSC0371-1 was chosen for transforming Aspergillus oryzae MT3568. A. oryzae MT3568 is an amdS (acetamidase) disrupted gene derivative of Aspergillus oryzae JaL355 (WO 2002/40694) in which pyrG auxotrophy was restored by inactivating the A. oryzae amdS gene. Protoplasts of A. oryzae MT3568 were prepared according to the method described in European Patent, EP0238023, pages 14-15.

E. coli 3701 containing pKKSC0371-1 was grown overnight according to the manufacturer's instructions (Genomed) and plasmid DNA of pKKSC0371-1 was isolated using a Plasmid Midi Kit (Genomed JETquick kit, cat.nr. 400250, GENOMED GmbH, Germany) according to the manufacturer's instructions. The purified plasmid DNA was transformed into Aspergillus oryzae MT3568. A. oryzae MT3568 protoplasts were prepared according to the method of Christensen et al., 1988, Bio/Technology 6: 1419-1422. The selection plates consisted of COVE sucrose with +10 mM acetamide+15 mM CsCl+TRITON® X-100 (50 µl/500 ml). The plates were incubated at 37° C. Briefly, 8 uls of plasmid DNA representing 3 ugs of DNA was added to 100 uls MT3568 protoplasts. 250 ul of 60% PEG solution was added and the tubes were gently mixed and incubate at 37⁰ for 30 minutes. The mix was added to 10 ml of pre melted Cove top agarose (The top agarose melted and then the temperature equilibrated to 40 C in a warm water bath before being added to the protoplast mixture). The combined mixture was then plated on two Cove-sucrose selection petri plates with 10 mM Acetamide. The plates are incubated at 37° C. for 4 days. Single Aspergillus transformed colonies were identified by growth on the selection Acetimide as a carbon source. Each of the four A. oryzae transformants were inoculated into 750 µl of YP medium supplemented with 2% glucose and also 750 µl of 2% maltodextrin and also DAP4C in 96 well deep plates and incubated at 37° C. stationary for 4 days. At same time the four transformants were restreaked on COVE-2 sucrose agar medium.

Culture broth from the Aspergillus oryzae transformants were then analyzed for production of the P34A98 GH30 polypeptide by SDS-PAGE using NUPAGE® 10% Bis-Tris SDS gels (Invitrogen, Carlsbad, Calif., USA) according to the manufacturer. A band at approximately 30 kDa was observed for each of the Aspergillus oryzae transformants. One A. oryzae transformant producing the P34A98 polypeptide was designated A. oryzae EXP09485.

A. oryzae EXP09485 was cultivated in 1000 ml Erlenmeyer shake flasks containing 100 ml of DAP4C medium at 26° C. for 4 days with agitation at 85 rpm.

Example 2

Characterization of the P34A98 GH30 Polypeptide Coding Sequence from Trichoderma harzianum O4

The genomic DNA sequence and deduced amino acid sequence of the Trichoderma harzianum O4 P34A98 GH30 polypeptide genomic coding sequence are shown in SEQ ID NO: 1 and SEQ ID NO: 2, respectively. The coding sequence is 1437 bp including the stop codon. The encoded predicted protein is 478 amino acids. Using the SignalP program (Nielsen et al., 1997, supra), a signal peptide of 20 residues was predicted. The mature protein contains 458 amino acids with a molecular mass of 52 kDa and a isoelectric point of 6.4. The discrepancy between the predicted molecular weight and the molecular weight by SDS gel analysis (65 kDa) most likely is the result of glycosylation of the peptide.

A comparative pairwise global alignment of amino acid sequences was determined using the Needleman and Wunsch algorithm (Needleman and Wunsch, 1970, supra) with a gap open penalty of 10, a gap extension penalty of 0.5, and the EBLOSUM62 matrix. The alignment showed that the deduced amino acid sequence of the *Trichoderma harzianum* O4 P34A98 GH30 polypeptide shares 90.17% identity (excluding gaps) to the deduced amino acid sequence of a GH30 polypeptide from Hypocrea_virens SWISSPROT_G9MWQ6.

Example 3

De-Glue Performance of 1,6-Endo-Beta-Galactanase in Liquid Detergent with Dirt Added
Preparation of Biofilm Swatches One strain of *Brevundimonas* sp. isolated from laundry biofilm was used in the present example. *Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB (Tryptone Soya broth, Oxoid) and incubated for 16 hours at 30° C. with shaking (240 rpm). After propagation, *Brevundimonas* sp. was pelleted by centrifugation (Sigma Laboratory Centrifuge 6K15) (3000 g at 21° C. in 7 min) and re-suspended in 10 mL of TSB diluted twice with milliQ water. Optical density (OD) at 600 nm was measured using a spectophometer (POLARstar Omega (BMG Labtech, Ortenberg, Germany). Fresh TSB diluted twice with milliQ water was inoculated to $OD_{600\,nm}$ 0.03, and 19 mL was added into 9 cm petri dishes (low dish NUNC 263991) in which squared swatches (5×5 cm) of sterile Polyester WFK30A was placed. After 72 h incubation at 15° C. with shaking (100 rpm), swatches are removed from the dishes placed on bench coat paper for overnight drying.
Deposition Wash Experiment Based on Wash TOM Assay Described Above:

Two dried biofilm swatches (with *Brevundimonas* sp) were mixed with two tracer swatches: ~7 g 50%/50% sterile Polyester WFK30A and sterile Cotton WFK10A swatches were used per TOM beaker (Terg-O-tometer (TOM) described under wash assays above). TOM beaker was prepared with 600 mL of wash liquor prepared by adding 3.33 g/l in water of a model detergent A. To the wash liquor 0.7 g/L soil (Pigmentschmutz, 09V, wfk, Krefeld, Germany) was added. The rotor was started in the Terg-O-Tometer 150 rpm for 10 minutes to complete dissolution of the dirt. Stop rotation. Start one beaker at a time by adding ballast (up till 10 g of 50% cotton wfk10A and polyester wfk30A) plus the two biofilm swatches per beaker plus 5×5 cm polyester wfk30A and Cotton 10A tracer swatches. The rotation in the Terge-o-tometer (TOM) was started on 110 rpm. Total wash time is 35 min at 30° C.

Test Conditions Example 3

Three beakers were added (0.05 ppm; 0.1 ppm or 0.2 ppm) 1,6 endo beta-Galactanase. In parallel was run a test with an enzyme preparation comprising 1,6 beta-endo Galactanase of 0.20 ppm as well as a test with an endo glucanase Celluclean® (supplied by Novozymes A/S). Control washes were without enzyme added as well as a wash without biofilm added.

Rinse: After wash the wash liquor is discarded and the swatches were rinsed in the beaker 2 times, 5 minutes each, with 350 ml fresh tap water each time. The swathes were hand wrenched and the ballast swatches from each beaker were discarded. Tracer and biofilm swatches are placed on a filter paper and left for drying overnight in dark drying chamber. Remission at 460 nm is measured on each of the swatches.
Result:

The wash tests show that a biofilm on a swatch can glue dirty particulate soil to the surface. This can be interpreted by the result of test in the reference wash without enzymes added. In this experiment dirt is added to the wash liquor and then there will be deposition to textile according to the type and general receptiveness. In the beaker washed without biofilm added we read the back ground deposition to 73 $Rem_{460\,n}$ units on the polyester Tracer (wash 7). If a biofilm is present on the textile surface then there will be extra dirt uptake due the stickiness. This is measured in the wash where biofilm is added without any enzymes added (Wash 1). The whiteness of the biofilm swatch is to 56 $Rem_{460\,n}$ units (wash 1), which is very gray. If 0.05 ppm 1,6 endo beta Galactanse (wash 4) is added then the grayness due to dirt-uptake is lowered to 62 $Rem_{460\,nm}$ units and increasing the dose to 0.10 ppm (wash 3) also increase the whiteness to 64 $Rem_{460\,n}$ units and 0.2 ppm (wash 2) increase to 66 $Rem_{460\,n}$ units. When comparing the performance with an enzyme preparation comprising 1,6-endobeta-galactanse (0.2 ppm). The enzyme preparation also inhibits the dirt deposition to 65 $Rem_{460\,n}$ units. Washing with endoglucanase (Celluclean®) also gives small but visible effect on the biofilm swatches as well as inhibition of cross contamination of sticky biofilm residues to the cotton fabric. The Galactanase also inhibit the cross contamination to both cotton tracer and polyester tracer when added at 0.2 ppm, here the polyester swatch is 74 $Rem_{460\,n}$ units and the cotton tracer swatch is 71 this is same level as if biofilm was not present in the wash.

| | | Remission 460 nm | | | | | |
|---|---|---|---|---|---|---|---|
| | | Wash 1 Model A detergent | Wash 2 0.2 ppm 1.6 beta endo galactanse | Wash 3 0.1 ppm 1.6 beta endo galactanse | Wash 4 0.05 ppm 1.6 beta endo galactanse | Wash 5 0.2 ppm enzyme preparation | Wash 6 2 ppm Celluclean | Wash 7 Model A detergent without biofilm swatch |
| *Brevundimonas* Biofilm swatch | AVG | 56 | 66 | 64 | 62 | 65 | 58 | |
| | STDEV | 1 | 1 | 1 | 2 | 2 | 0 | |
| Polyester tracer | AVG | 72 | 74 | 73 | 73 | 73 | 73 | 73 |
| | STDEV | 0 | 0 | 1 | 1 | 1 | 0 | 0 |

-continued

| | | Wash 1 Model A detergent | Wash 2 0.2 ppm 1.6 beta endo galactanse | Wash 3 0.1 ppm 1.6 beta endo galactanse | Wash 4 0.05 ppm 1.6 beta endo galactanse | Wash 5 0.2 ppm enzyme preparation | Wash 6 2 ppm Celluclean | Wash 7 Model A detergent without biofilm swatch |
|---|---|---|---|---|---|---|---|---|
| | | | | Remission 460 nm | | | | |
| Cotton tracer | AVG | 67 | 71 | 69 | 68 | 70 | 70 | 70 |
| | STDEV | 0 | 1 | 1 | 1 | 1 | 0 | 0 |

Example 4

Enzyme Performance on Biofilm of *Corynebacterium*
Preparation of Biofilm Swatches One strain of *Corynebacterium xerosis* isolated from laundry biofilm was used in the present example. *Corynebacterium xerosis* was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB (Tryptone Soya broth, Oxoid) and incubated for 16 hours at 30° C. with shaking (240 rpm). After propagation, *Corynebacterium xerosis* was pelleted by centrifugation (Sigma Laboratory Centrifuge 6K15) (3000 g at 21° C. in 7 min) and resuspended in 10 mL of TSB diluted twice with milliQ water. Optical density (OD) at 600 nm was measured using a spectophometer (POLARstar Omega (BMG Labtech, Ortenberg, Germany). Fresh TSB diluted twice with milliQ water was inoculated to $OD_{600\ nm}$ 0.03, and 19 mL was added into 9 cm petri dishes (low dish NUNC 263991) in which squared swatches (5×5 cm) of sterile Polyester WFK30A was placed. After 72 h incubation at 30° C. with shaking (100 rpm), swatches are removed from the dishes placed on bench coat paper for overnight drying then there will be deposition to textile according to the type and general receptiveness. In the beaker (wash 7) from example 3, washed without biofilm added we read the back ground deposition to 73 $Rem_{460\ n}$ units on the polyester Tracer. If a biofilm is present on the textile surface then there will be extra dirt uptake due the stickiness. This is measured in the wash where biofilm is added without any enzymes added (Wash 1). The whiteness of the biofilm swatch is to 61 $Rem_{460\ n}$ units (wash 1). If 0.2 ppm 1,6 endo beta Galactanse (wash 2) is added then the grayness due to dirt-uptake is lowered to 67 $Rem_{460\ nm}$ units and increasing the dose to 1.0 ppm (wash 3) also increase the whiteness to 70 $Rem_{460\ n}$ Units. We compare the performance with an enzyme preparation comprising 1,6 endo beta Galactanse (wash 4). The enzyme preparation added in 3 ppm also inhibits the dirt deposition to 70 $Rem_{460\ n}$ units. Washing with endoglucanase (Celluclean®) do not give visible effect on the biofilm swatches. Cross contamination of *Corynebacterium xerosis* to otherwise clean textile is very low. Celluclean have small tendency to prevent cross contamination to cotton and 1,6 endo beta Galactanse in 1.0 ppm have small tendency to give small reduction of cross contamination to polyester. This is also the case for the enzyme preparation.

| | | Wash 1 No enzyme | Wash 2 0.2 ppm 1.6 beta endo galactanase | Wash 3 1.0 ppm 1.6 beta endo galactanase | Wash 4 3 ppm enzyme preparation | Wash 5 3 ppm Celluclean 5.0 T |
|---|---|---|---|---|---|---|
| | | | | Remission 460 nm on | | |
| *Brevundimonas* | AVG | 61 | 67 | 70 | 70 | 62 |
| Biofilm swatch | STDEV | 0 | 1 | 1 | 0 | 0 |
| Polyester tracer | AVG | 71 | 73 | 73 | 74 | 71 |
| | STDEV | 0 | 0 | 0 | 0 | 0 |
| Cotton tracer | AVG | 70 | 70 | 71 | 71 | 72 |
| | STDEV | 1 | 1 | 0 | 1 | 1 |

Washing was carried out as described in the deposition wash experiment described in example 3 but with the following conditions: Three beakers were added (0.05 ppm; 0.1 ppm or 0.2 ppm) 1,6 endo beta-Galactanase. In parallel was run a test with an enzyme preparation comprising 1,6 beta-endo Galactanase of 0.20 ppm as well as a test with an endo glucanase Celluclean® (supplied by Novozymes A/S). Control washes were without enzyme added as well as a wash without biofilm added. The rinsing was carried out as described in example 3.

Result:

The wash tests show that a biofilm on a swatch can glue dirty particulate soil to the surface. This can be interpreted by the result of test in the reference wash without enzymes added. In this experiment dirt is added to the wash liquor and Example 5

The preparation of Biofilm swatches and the deposition washing was carried out as described in example 3. With regard to the wash conditions, a protease (Savinase® (SEQ ID NO 7) supplied by Novozymes A/S) was added in addition to the 11,6-endo-beta-galactanase.

In wash 1 no enzyme was added and this gave a deposition to the biofilm swatch to the level of 61 $Rem_{460\ n}$ units. In wash 2 0.025 ppm 1,6-endo-beta-galactanase was added which reduced the deposition slightly to 63 $Rem_{460\ n}$ units. In wash 3 0.1 ppm was added and this reduced the deposition to the level of 68 $Rem_{460\ n}$ units which is a very visible difference. In wash 4, 0.3 ppm 1,6-endo-beta-galactanase was added and this resulted in a reduction of deposition to 70 Rem$_{460\ n}$ units. Wash 5 was a combination of the low galactanase dosage og 0.025 ppm and 50 nM Savinase® this increased the reduction that we found in wash 2 (0.025 ppm 1,6-endo-beta-galactanase alone) from 63 to 67 Rem$_{460\ n}$ units and the same pattern was seen in was 6 and 7 where we added 0.1 ppm and 0.3 ppm galactanase together with 50 nM Savinase®. These two washes reduced the deposition to 71 and 72 Rem$_{460\ n}$ units respectively which are close to the background deposition to clean polyester tracer as seen in example 3 wash 7. This shows that the 1,6-endo-beta-galactanase wash performance can be boosted by adding Savinase.

|  |  | Rem$_{460\ n}$ units | | | | | | |
|---|---|---|---|---|---|---|---|---|
|  |  | wash 1 | wash 2 | wash 3 | wash 4 | wash 5 | wash 6 | wash 7 |
|  |  |  | 1.6 beta endo galactase | | | | | |
|  |  | 0 | 0.025 ppm | 0.1 ppm | 0.3 ppm | 0.025 ppm | 0.1 ppm | 0.3 ppm |
|  |  |  |  |  |  | Savinase | | |
|  |  | 0 | 0 | 0 | 0 | 50 nM | 50 nM | 50 nM |
| *Brevundimonas* | AVG | 61 | 63 | 68 | 70 | 67 | 71 | 72 |
| Biofilm swatch | STDEV | 0 | 0 | 1 | 0 | 0 | 0 | 1 |
| Polyester tracer | AVG | 73 | 73 | 74 | 74 | 73 | 72 | 74 |
|  | STDEV | 1 | 1 | 0 | 0 | 0 | 0 | 0 |
| Cotton tracer | AVG | 66 | 66 | 69 | 69 | 65 | 68 | 70 |
|  | STDEV | 2 | 1 | 1 | 1 | 0 | 0 | 1 |

Example 6

Preparation of Biofilm Swatches

One strain of *Brevundimonas* sp. isolated from laundry biofilm was used in the present example. *Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 16 hours at 30° C. with shaking (240 rpm). After propagation, *Brevundimonas* sp. was pelleted by centrifugation (Sigma Laboratory Centrifuge 6K15) (3000 g at 21° C. in 7 min) and re-suspended in 10 mL of TSB diluted twice with milliQ water. Optical density (OD) at 600 nm was measured using a spectophometer (POLARstar Omega (BMG Labtech, Ortenberg, Germany). Fresh TSB diluted twice with milliQ water was inoculated to OD$_{600\ nm}$ 0.03, and 19 mL was added into 9 cm petri dishes (low dish NUNC 263991) in which squared swatches (5×5 cm) of sterile Polyester WFK30A was placed. After 72 h incubation at 15° C. with shaking (100 rpm), swatches are removed from the dishes placed on bench coat paper for overnight drying.

Washing Experiment:

Two dried biofilm swatches (with *Brevundimonas* sp) were mixed with two tracer swatches: 7 g 50%/50% sterile Polyester WFK30A and sterile Cotton WFK10A swatches to a total of 10 g textile were used per TOM beaker. TOM beaker was prepared with 600 mL of wash liquor prepared by adding 3.33 g/l in water of a model detergent A. To the wash liquor 0.7 g/L soil (Pigmentschmutz, 09V, wfk, Krefeld, Germany) was added. The rotor was started in the Terg-O-Tometer 150 rpm for 10 minutes to complete dissolution of the dirt. Stop rotation. Start one beaker at a time by adding ballast (up till 10 g of 50% cotton wfk10A and polyester wfk30A) plus two biofilm swatches per beaker plus 3.5×3.5 cm polyester wfk30A and Cotton 10A Tracer swatches. The rotation in the Terge-o-tometer (TOM) was started on 110 rpm. Total wash time is 35 min at 30° C. Two beakers were added (1.0 ppm and 0.5 ppm) enzyme preparation, one beaker wash added bleach (0.09 g TAED (N,N, N',N'-Tetraacetylethylenediamine, Cas No. 10543-57-4, Aldrich) plus 0.407 g NaHCO$_3$ (Sodium Carbonate Peroxyhydrate, CAS No 15630-89-4)), one beaker was added 1.0 ppm enzyme preparation plus bleach, another beaker was added 0.5 ppm enzyme preparation plus bleach. Control washes were without enzyme added as well as a wash without biofilm swatch added.

After wash the wash liquor is discarded and the swatches were rinsed in the beaker 2 times, 5 minutes each, with 350 ml fresh tap water each time. The swathes were hand wrenched and the ballast swatches from each beaker were dried in a labeled wash bag. Tracer and biofilm swatches are placed on a filter paper and left for drying overnight in dark drying chamber Remission at 460 nm is measured on each of the swatches. The biofilm swatches were discarded.

A new wash with same wash conditions for each beaker was initiated the day after. The tracers from each wash condition were used again plus two new tracers of wfk30A as well as wfk10A plus new fresh biofilm swatches with *Brevundimonas* wash added. Most of the ballast from the former wash was reused. The weight from the new tracers were subtracted from the weight of ballast—which means that the total amount of textile used for each wash cycle was constant (10 gram). These wash conditions was repeated 9 times.

Remission was Measure for Cotton Tracer Swatches wfk10A

| Rem$_{460n}$ units | Beaker 1 | Beaker 2 | Beaker 3 | Beaker 4 | Beaker 5 | Beaker 6 | Beaker 7 | Beaker 8 | Beaker 9 | Beaker 10 |
|---|---|---|---|---|---|---|---|---|---|---|
| Enzyme preparation | ÷ | ÷ | 0.5 ppm | 1 ppm | 0.5 ppm | 1 ppm | ÷ | 1 ppm | ÷ | 1 ppm |
| Bleach | ÷ | + | + | + | ÷ | ÷ | ÷ | ÷ | + | + |
| Biofilm Swatch | + | + | + | + | + | + | ÷ | ÷ | ÷ | ÷ |
| Wash 1 | 69 | 67 | 69 | 69 | 69 | 69 | 69 | 69 | 69 | 70 |
| Wash 2 | 63 | 65 | 67 | 67 | 67 | 67 | 67 | 68 | 68 | 68 |
| Wash 3 | 60 | 62 | 66 | 66 | 65 | 64 | 65 | 65 | 67 | 67 |

| Rem$_{460n}$ units | Beaker 1 | Beaker 2 | Beaker 3 | Beaker 4 | Beaker 5 | Beaker 6 | Beaker 7 | Beaker 8 | Beaker 9 | Beaker 10 |
|---|---|---|---|---|---|---|---|---|---|---|
| Wash 4 | 58 | 61 | 65 | 65 | 63 | 63 | 65 | 65 | 66 | 66 |
| Wash 5 | 56 | 59 | 64 | 65 | 62 | 62 | 63 | 63 | 65 | 65 |
| Wash 6 | 55 | 57 | 62 | 63 | 60 | 61 | 62 | 62 | 63 | 64 |
| Wash 7 | 55 | 57 | 62 | 63 | 60 | 60 | 62 | 62 | 64 | 64 |
| Wash 8 | 53 | 55 | 60 | 62 | 57 | 58 | 60 | 60 | 62 | 62 |
| Wash 9 | 51 | 53 | 59 | 61 | 56 | 57 | 60 | 59 | 61 | 61 |
| Wash 10 | 48 | 50 | 57 | 59 | 53 | 55 | 57 | 57 | 59 | 59 |

Before start of experiment the cotton Tracers was pre-washed in order to remove textile finishing material. This gave a Remission of 460 nm of 74 Rem$_{460\ n}$ units. All washes was done as Deposition wash as described in example 3. Beaker 1 is a wash condition where biofilm is present but no enzyme and no bleach. When these conditions were carried out 10 times the cotton tracers entailed a fall in whiteness on the wfk10A cotton tracers from 74 Rem$_{460\ n}$ units to 48 Rem$_{460\ n}$ units.

In beaker 7, we did not add biofilm swatch or enzyme or bleach in any of the 10 repeated washes. This showed the background deposition on the clean textile. After 10 wash cycles it is on 57 Rem$_{460\ n}$ units. Compared to beaker 1 there was a difference of 9 Rem$_{460\ n}$ units on the cotton tracer after 10 wash cycles due to cross contamination of biofilm material together with dirt of the tracer swatches in beaker 1.

In beaker 5 conditions, biofilm swatch, no bleach but 0.5 ppm enzyme preparation comprising 1,6 beta-endo-Galactanase were added to each wash cycle. This reduced the deposition on the cotton tracers to 53 Rem$_{460\ n}$ units.

Beaker 6 conditions (biofilm, no bleach, 1 ppm enzyme preparation) gave a reduction of deposition after 10 wash cycles to 55 Rem$_{460\ n}$ units. Beaker 10 condition (no biofilm, no bleach, 1 ppm enzyme preparation) test if enzyme can influence the background deposition (measured in Beaker 1 conditions). The result shows that adding enzyme without biofilm present did not give any difference in deposition to cotton tracer. The difference of deposition on the cotton tracers between beaker condition 1 and condition 5 and 6 is due to that the enzyme de-gluing effects of biofilm matrix. It is believed that during wash pieces of the biofilm matrix are freed from the biofilm surface of the biofilm swatch and when it deposits on the textile surfaces on the tracer it also withdraws the dirt from the washing solution. The experiment shows that the enzyme preparation can reduce the deposition to the level of a biofilm free wash (beaker condition 7). The end points of the different wash conditions mirror the approximate pattern of deposition from wash cycle to wash cycle. Beaker 2 conditions (biofilm swatch, bleach no enzyme) showed that after 10 washes the deposition to cotton tracers resulted in 50 Rem$_{460\ n}$ units which is a slight reduction from the beaker 1 condition (biofilm swatch, no bleach and no enzyme) but far from the reduction that the enzyme preparation gave. If we combined bleach and enzyme preparation as done in beaker condition 3 and 4 we saw a synergistic effect The reduction of deposition to cotton tracers was reduced to 57 Rem$_{460\ n}$ units for condition 3. This resembles the results from beaker condition 7 where no biofilm wash present. The higher enzyme dosage together with bleach (beaker condition 4) gave a slight increase compared to beaker condition 7. It resembles what happens in beaker condition 9 (no biofilm, no enzyme, bleach) and 10 (no biofilm, 1 ppm enzyme, bleach). Beaker 5 and 6 shows what the enzyme can do alone (53 and 55 rem units at high and low dosage) and beaker 2 shows what bleach can do alone (50 rem units). If the function of bleach and galactanase was additive we could have expected results like 55 and 57 rem units (for high and low enzyme dosage) in a wash where they are combined but actually we get 57 and 59 rem units (for low and high enzyme dosage) which is a synergisitic result. The beaker condition 9 shows that bleach have a small inhibition on the background deposition to clean textile, which is kept whether there is enzyme present (condition 10) or not. This indicates that bleach may have impact on the dirt so that it does not deposit in the same degree. It also indicates that the enzyme preparation and bleach can inhibit deposition by different mechanisms.

Example 7

Deep-Cleaning Performance of Enzyme Preparation Comprising 1,6-Endo-Beta-Galactanase in Liquid Detergent Over 2 Washes One strain of *Brevundimonas* sp. isolated from laundry was used in the present example. *Brevundimonas* sp. was pre-grown on Tryptone Soya Agar (TSA) (pH 7.3) (CM0131; Oxoid Ltd, Basingstoke, UK) for 2-5 days at 30° C. From a single colony, a loop-full was transferred to 10 mL of TSB and incubated for 16 hours at 30° C. with shaking (240 rpm). After propagation, *Brevundimonas* sp. was pelleted by centrifugation (Sigma Laboratory Centrifuge 6K15) (3000 g at 21° C. in 7 min) and resuspended in 10 mL of TSB diluted twice with milliQ water. Optical density (OD) at 600 nm was measured using a spectophometer (POLARstar Omega (BMG Labtech, Ortenberg, Germany). Fresh TSB diluted twice with milliQ water was inoculated to OD$_{600\ nm}$ 0.03, and 1.6 mL was added into each well of a 12-well polystyrene flat-bottom microplate (3512; Corning Incorporated, Corning, N.Y., USA), in which round swatches (diameter 2 cm) of sterile Polyester WFK30A was placed. After 24 h and 72 h incubation, respectively, at 15° C. with shaking (100 rpm), swatches were rinsed twice with 0.9% (w/v) NaCl.

In wash 1, five rinsed swatches with *Brevundimonas* sp. was mixed with five sterile Polyester WFK30A swatches in a 50 mL test tube (described in wash assay mini-LOM above) and added 10 mL of wash liquor prepared by adding 3.33 g/l in water of a model detergent A and enzyme preparation comprising 1,6-endobeta-galactanse (0.3 ppm). Washes with model detergent A not added the enzyme preparation comprising 1,6-endobeta-galactanse was made in parallel. Test tubes were placed in a Stuart rotator for 1 hour at 30° C. Swatches were rinsed twice with tap water and dried on filter paper over night.

In wash 2, five dried swatches were washed in a 50 mL test tube added 10 mL of wash liquor prepared by adding 3.33 g/l in water of a model detergent A and 0.7 g/L soil (Pigmentschmutz, 09V, wfk, Krefeld, Germany). Test tubes were placed in a Stuart rotator for 1 hour at 30° C. Swatches were rinsed twice with tap water and dried on filter paper over night. Remission (L values) was measured using a Color Eye (Macbeth Color Eye 7000 reflectance spectrophotometer). The measurements were made without UV in the incident light, and the L value from the CIE Lab color space was extracted. Data is represented as Delta L values meaning the L value of the swatch washed with enzyme preparation comprising 1,6-endobeta-galactanse minus the L value of swatch washed without enzyme preparation comprising 1,6-endobeta-galactanse.

The table shows the deep-cleaning effects of an enzyme preparation comprising 1,6-endobeta-galactanse

|  | 24 h *Brevundimonas* stain | | 72 h *Brevundimonas* stain | |
| --- | --- | --- | --- | --- |
|  | Donor | Tracer | Donor | Tracer |
| Remission (ΔL) | 3.9 | 1.7 | 2.2 | 5.4 |

| | Color difference | | | | | |
| --- | --- | --- | --- | --- | --- | --- |
|  | $L_{Donor+enz.}$ | $L_{Donor-enz.}$ | (ΔL) | $L_{Tracer+enz.}$ | $L_{Tracer-enz.}$ | (ΔL) |
| 24 h *Brevundimonas* stain | 90.6 | 86.7 | 3.9 | 93.0 | 91.2 | 1.7 |
| 72 h *Brevundimonas* stain | 87.2 | 85.0 | 2.2 | 91.9 | 86.5 | 5.4 |

Example 8

Performance of Enzyme Preparation Comprising 1,6-Endo-Beta-Galactanase in MiniLOM Wash Preparation of Biofilm Swatches For preparation of biofilm a *Brevundimonas vesicularis* strain was taken from a −80° C. freeze culture and plated out on TSA (tryptone Soy agar) plates. After 3 days 4 tubes with 10 mL TSB (Tryptone Soy Broth) (from Oxoid) was inoculated with bacteria culture from the plates. The TSB tubes were thoroughly mixed by whirl mixer before they were incubated overnight at 30° C. with shaking applied at 200 rpm. The overnight culture was then collected in a 50 ml centrifuge tube and centrifuged at 3000 rpm for 5 min. the supernatant was discarded and the pellet was dissolved in 5 ml TSB per tube (20 ml in total). 150 ml of the culture was diluted 10× with 1350 µl 100% TSB in an Eppendorf tube. A 20× dilution was made by taking 500 µl of the 10× dilution to 500 µl 100% TSB in an Eppendorf tube. 4×100 µL of the 10× and 20× dilutions and blank (100% TSB) was added to a 96 brønd nunc micro titter plate. The plate was measured at 600 nm on Fluostar Omega securing that one of the dilutions was below 0.6. The OD600 of the Overnight culture was determined and diluted to an OD Of 0.03 in 50% TSB. Prewashed Wfk 30A PO (Standard polyester WFK 30 A (WFK)) was cut in circular swatches with a 2 cm diameter and placed in autoclave bags and autoclaved at the "liquid program" on the Systec autoclave with 121° C. in 15 min and then cooling down to 80 before it is opened. Sterile 30A (Standard polyester WFK 30 A (WFK)) swatch was transferred with a sterile tweeze to each well in a 12 well micro titter plate. 1.62 ml of the diluted O/N culture was added to each of the well. The swatches was incubated at 15° C. with 70 rpm shaking applied for overnight on a Innova 2100 Platform shaker. After incubation in 24 h the swatches was rinsed 2× in 3 ml 0.9% NaCL. The swatches were used immediately after the rinse for wash trial. Preparation method for PO (polyester) tracers: Pre washed Wfk 30A (Standard polyester WFK 30 A (WFK)) is cut in circular swatches with a diameter of 2 cm. The swatches were marked by a sizzer cut to differentiate them from the 1 day biofilm swatches after the washes.

Preparation of "Dirty Detergent": Weigh of the 3.33 g Model A detergent in a weighing boat add 0.7 g add 09 V (09 V standard pigment soil from WFK; wfk Testgewebe GmbH, Christenfeld 10, D-41379 Brüggen, Deutschland) pigment soil on top of the Model A detergent. This was done in a fume hood using disposable gloves. The weighing boat was added to 1 L of 15° dH water. The soil was dissolved at maximum speed for at least 10 minutes, to dissolve the soil completely.

Washing Method

Turn on a heating cabinet to 30° C. Prepare 1 l of Dirty detergent according to "Dirty Detergent" preparation method. Into 50 mL Plastic tubes, which each tube represented a wash, five circular (2 cm diameter) biofilm swatches, prepared as described above were added to the beakers Five circular (2 cm diameter) clean pieces of PO (tracers) were added to each of the tubes. Enzymes were prepared and kept on ice. 10 ml of "Dirty detergent" (see preparation method) was added to the first tube and enzymes added immediately after. The lid was then added to the tube, and the tube was put on the Mini-LOM rotator (Stuart Rotator SB3). Rotation speed of MiniLOM rotator was 20 rpm. When the first tube was placed on the Mini-LOM rotator the time measurement of the wash was started. Dirty detergent and enzymes were then added to the other tubes, and placed on the Rotator. When all of the tubes were added to the Rotator, it was placed the 30° C. heating cabinet for 60 minutes from the time that the lid was added to the first tube. Rinse procedure was done by removing the rotator from the cabinet and placing it on the operating table with the rotation on. Tube no 1 was taken and the wash water discarded with the swatches left behind in the tubes. 20 ml of 15° dH was added to the tube and it was added back to the rotator. This was then done for all the test tubes in the trial. The rinse was done at ambient room temperature for 10 minutes. A second rinse was done repeating the above described steps. After the second wash the swatches were removed from each of the tubes and added to a piece of paper and dried overnight at room temperature in darkness. Evaluation was done by photographing the swatches in Verivide and analyzed by the software Digieye V2.62. The Y-values were used to present the data.

$$Y=\int_0^\infty I(\lambda)\bar{y}(\lambda)d\lambda.$$

where Y is the lightness signal in the tristimulus values scale.

Textile prewash procedure:

A Miele Softtronic W2245 washing machine was used to prepare textile with a prewash. 73.36 g ECE-2 color fastness detergent from WFK, version without CMC, optical brightener and enzyme was weighed out into a wash ball. 2.8 g the commercially available amylase, Stainzyme® 12 L (Novozymes A/S) and 3.5 g commercially available cellulase Celluclean® (Novozymes A/S) 4500 T was added into the wash ball on top of the detergent and the ball was placed in the bottom of the drum. Textile was cut into 1.0×1.0 meters and the load was filled up till 3.0 kg with 50/50% PO/cotton mixed ballast items (pillowcases, shirts and tea towels) and placed into the machine. Water of 15° dH Ca/Mg/CO3 ration 4:1:7.5 was used for the wash. Standard wash program for cotton wash was used at 40° C. This wash was followed by another prewash using same program, temperature, water-hardness, detergent and Stainzyme® 12 L (commercially available from Novozymes) dosing but this time without Celluclean®. This wash is then followed by another wash cycle with the same conditions as the two other prewashes and now leaving out all enzymes. After the last wash the textile is line dried overnight at room temperature. The textile is now ready for use as tracer and biofilm material.

Dose:
1,6 endo beta galactanase (GH30_5) from *T. harzianum* was used in a dose response of 0.5; 2.0; 5.0 and 10.0 mg ep/L and compared with a wash without enzyme added.

|  | Clean prewashed polyester wfk 30A Y Value |
|---|---|
| AVG | 88.0 |
| STDEV | 0.5 |

The table above shows that there is a very distinct effect to wash biofilm in dirty detergent.

When the 1,6 ß-endo galactanase from *T harzianum* is present in a wash it has pronounce de-gluing capability of the biofilm of 6-9 Y values dependent on the dosage. A Y-value of 2 can be clearly distinguished by the human eye. There is a max response between 0, 5 and 2 mg ep/L of 8-9 Y values. Adding higher enzyme concentration does not give higher response in this case but the max whiteness of wash is nearly reached at 2 mg ep/L. Transfer of soil and biofilm material between biofilm donor swatches and tracers was very limited and washing performance with enzyme is correspondingly low. Delta Y-value lies within the standard deviation.

Clean prewashed PO (polyester) has a Y-value of 88. This textile has not been washed in Dirty detergent and has the maximal attribute of whiteness for this textile. When we compare the tracers washed in Dirty detergent with biofilm donor swatches present. Uptake of dirt is 7 rem units. The tracers are washed together with biofilm containing donor swatches. During wash there can be cross-contamination of bacteria and biofilm. The cross contamination can be visualized by the dirt uptake in the wash with Dirty detergent.

Wash Example 1

|  | Y values biofilm swatches |  |  |  |  | delta Y-value (with enz-blank) biofilm swatches |  |  |  |
|---|---|---|---|---|---|---|---|---|---|
|  | Blank | Galactanase 0.5 0.5 mg/L | Galactanase 2.0 mg/L | Galactanase 5.0 mg/L | Galactanase 10.0 mg/L | Galactanase 0.5 0.5 mg/L | Galactanase 2.0 mg/L | Galactanase 5.0 mg/L | Galactanase 10.0 mg/L |
| AVG | 67.2 | 73.2 | 76.5 | 75.4 | 76.3 | 6.1 | 9.3 | 8.2 | 9.1 |
| STDEV | 1.1 | 0.7 | 0.7 | 1.3 | 0.8 | . | . | . | . |

|  | Y values Polyester tracers |  |  |  |  | delta Y-value (with enz-blank) biofilm swatches |  |  |  |
|---|---|---|---|---|---|---|---|---|---|
|  | Blank | Galactanase 0.5 0.5 mg/L | Galactanase 2.0 mg/L | Galactanase 5.0 mg/L | Galactanase 10.0 mg/L | Galactanase 0.5 0.5 mg/L | Galactanase 2.0 mg/L | Galactanase 5.0 mg/L | Galactanase 10.0 mg/L |
| AVG | 75.4 | 75.3 | 75.0 | 76.9 | 76.3 | 0 | 0 | 1.3 | 0.9 |
| STDEV | 1.0 | 1.7 | 1.0 | 1.0 | 1.4 | . | . | . | . |

Wash Example 2: this wash is done the same way as example 1 but with enzyme dosages of 1 and 10 mg ep/L. Blank values between examples 1 and 2 shows that there is a difference of 4 Y-values between the two batches. This is also mirrored in the washing results. The absolute values of Y for the enzyme treated swatches in example 2 are similar but the delta Y is 4 Y units lower. Reason is that the biofilm is less mature in example 2. The 1,6 endo R-galactanase can give nice washing benefits at both dosages. 10 mgep/L gives about double Y-values than 1 mg ep/L. Performance on tracers are within the STDEV so it cannot be interpreted.

Wash Example 2

|  | Y values biofilm swatches |  |  | Y values tracers (clean PO) |  |  | delta Y-value (with enz-blank) biofilm swatches |  | Y-values |  |
|---|---|---|---|---|---|---|---|---|---|---|
|  | Blank | Galactanase 1.0 mgep/L | Galactanase 10.0 mgep/L | blank | Galactanase 1.0 mgep/L | Galactanase 10.0 epmg/L | Galactanase 1.0 mgep/L | Galactanase 10.0 mgep/L | Galactanase 1.0 mgep/L | Galactanase 10.0 mgep/L |
| AVG | 71.0 | 74.7 | 77.3 | 80.7 | 80.7 | 81.5 | 3.6 | 6.3 | 0.0 | 0.8 |
| STDEV | 0.9 | 0.8 | 1.1 | 0.9 | 1.7 | 1.4 | . | . | . | . |

The invention claimed is:

1. A detergent composition comprising a polypeptide having endo-beta-1,6-galactanase activity, a surfactant, and a detergent adjunct ingredient, wherein
   (a) the polypeptide having endo-beta-1,6-galactanase activity comprises an amino acid sequence having at least 94% sequence identity to the mature polypeptide of SEQ ID NO: 2;
   (b) the detergent adjunct ingredient is selected from the group consisting of builders, flocculating aid, chelating agents, dye transfer inhibitors, enzymes, enzyme stabilizers, enzyme inhibitors, catalytic materials, bleaching system, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments; and
   (c) the detergent composition is a stabilized liquid detergent, a powder detergent or a granule detergent;
   Wherein the composition reduces the amount of deposition of dirt onto a *Brevundimonas* biofilm swatch in a Tergometer wash assay compared to the amount deposited by an identical composition lacking the endo-beta-1,6-galactanase.

2. The detergent composition of claim 1, wherein the polypeptide having endo-beta-1,6-galactanase activity comprises an amino acid sequence having at least 95% sequence identity to the mature polypeptide of SEQ ID NO: 2.

3. The detergent composition of claim 1, wherein the polypeptide having endo-beta-1,6-galactanase activity comprises an amino acid sequence having at least 97% sequence identity to the mature polypeptide of SEQ ID NO: 2.

4. The detergent composition of claim 1, wherein the polypeptide having endo-beta-1,6-galactanase activity is the mature polypeptide of SEQ ID NO: 2.

5. The detergent composition of claim 1, wherein the surfactant comprises an anionic surfactant.

6. The detergent composition of claim 1, wherein the detergent adjunct ingredient is a builder.

7. The detergent composition of claim 1, wherein the detergent adjunct ingredient is a bleaching system.

8. The detergent composition of claim 7, wherein the bleaching system is selected from the group consisting of tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), 6-(phthalimido)peroxyhexanoic acid (PAP), NaHCO$_3$ and/or mixtures thereof.

9. The detergent composition of claim 7, wherein the bleaching system comprises a bleach catalyst selected from the group consisting of organic catalysts having the following formulae:

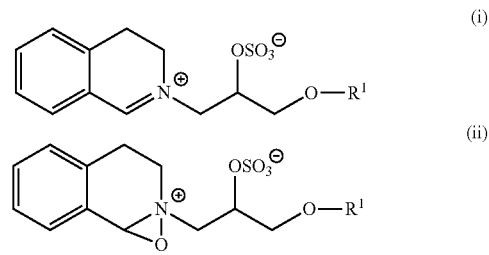

and mixtures thereof;
   wherein each R$^1$ is independently a branched alkyl group containing from 9 to 24 carbons or linear alkyl group containing from 11 to 24 carbons.

10. The detergent composition of claim 1, wherein the detergent adjunct ingredient is one or more enzymes selected from the group consisting of amylases, arabinases, carbohydrases, cellulases, cutinases, galactanases, lipases, mannanases, oxidases, pectinases, peroxidases, proteases, and xylanases.

11. The detergent composition of claim 10, wherein the enzyme is a protease.

12. The detergent composition of claim 11, wherein the protease is a serine protease or a metalloprotease.

13. The detergent composition of claim 11, wherein the protease is selected from the group consisting of subtilisin BPN', subtilisin Novo, subtilisin Carlsberg, subtilisin 309, subtilisin 147, subtilisin 168, *Bacillus lentus* DSM 5483 protease, trypsin-like proteases, proteases from *Fusarium* and variants thereof.

14. The detergent composition of claim 11, wherein the protease has at least 95% sequence identity to SEQ ID NO: 7.

15. The detergent composition of claim 1, which comprises the polypeptide having endo-beta-1,6-galactanase activity in an amount of 0.01 mg of endo-beta-1,6-galactanase protein per gram detergent composition.

16. The detergent composition of claim 1, which comprises the polypeptide having endo-beta-1,6-galactanase activity in an amount of 0.1 mg of endo-beta-1,6-galactanase protein per gram detergent composition.

17. A method for washing an item, comprising:
   a. exposing the item to a wash liquor comprising the detergent composition of claim 1; and
   b. completing at least one wash cycle; wherein the item is a textile, a dishware or a hard surface.

18. The method of claim 17, further comprising rising the item.

* * * * *

SEQUENCE LISTING

<160> NUMBER OF SEQ ID NOS: 8

<210> SEQ ID NO 1
<211> LENGTH: 1437
<212> TYPE: DNA
<213> ORGANISM: Trichoderma harzianum
<220> FEATURE:
<221> NAME/KEY: CDS
<222> LOCATION: (1)..(1434)
<220> FEATURE:
<221> NAME/KEY: sig_peptide
<222> LOCATION: (1)..(60)
<220> FEATURE:
<221> NAME/KEY: mat_peptide
<222> LOCATION: (61)..(1434)

<400> SEQUENCE: 1

```
atg cga tca gct att act cca tcg tta gcc ctt gct ctg ctg tcc caa       48
Met Arg Ser Ala Ile Thr Pro Ser Leu Ala Leu Ala Leu Leu Ser Gln
-20             -15                 -10                  -5 aca gct ggg gcc gat aca aca ctt tcc att gat ccc acc tct aat tgg       96
Thr Ala Gly Ala Asp Thr Thr Leu Ser Ile Asp Pro Thr Ser Asn Trp
            -1   1               5                   10 ggt acg tgg gaa ggc tgg ggt gta tct ctt gct tgg tgg gcg aaa gcc      144
Gly Thr Trp Glu Gly Trp Gly Val Ser Leu Ala Trp Trp Ala Lys Ala
         15                  20                  25 ttt ggc aac cga gat gac cta gcc aat gtc ttt ttc act agg aac aac      192
Phe Gly Asn Arg Asp Asp Leu Ala Asn Val Phe Phe Thr Arg Asn Asn
     30                  35                  40 caa gtc atc aat ggc cag aac ctg ccg ggc ttg ggc ttc aac att gct      240
Gln Val Ile Asn Gly Gln Asn Leu Pro Gly Leu Gly Phe Asn Ile Ala
 45                  50                  55                  60 cgg tac aat gcc ggc gca tgc agc acc aac acg tat aat ggc tcc agt      288
Arg Tyr Asn Ala Gly Ala Cys Ser Thr Asn Thr Tyr Asn Gly Ser Ser
                 65                  70                  75 atg gta gtc tcg tcg agt atc aag ccg tct cgg cag gtt gat ggt tac      336
Met Val Val Ser Ser Ser Ile Lys Pro Ser Arg Gln Val Asp Gly Tyr
             80                  85                  90 tgg ctc gat tgg gcc agc acc gac cct gct tca tcc agc tgg aac tgg      384
Trp Leu Asp Trp Ala Ser Thr Asp Pro Ala Ser Ser Ser Trp Asn Trp
         95                 100                 105 aat gtc gat gcc aac cag cga gcg atg tta caa aag gcc aaa gca aac      432
Asn Val Asp Ala Asn Gln Arg Ala Met Leu Gln Lys Ala Lys Ala Asn
     110                 115                 120 ggt gca aac atc ttt gag ctc ttc tcc aac tcg cct atg tgg tgg atg      480
Gly Ala Asn Ile Phe Glu Leu Phe Ser Asn Ser Pro Met Trp Trp Met
125                 130                 135                 140 tgc ctg aat cat aat ccg tcg gga agc ggc tcg agt gat aac ctt cag      528
Cys Leu Asn His Asn Pro Ser Gly Ser Gly Ser Ser Asp Asn Leu Gln
                 145                 150                 155 tca tgg aac tac caa aat cac gct gtt tat ctt gcc aat att gct caa      576
Ser Trp Asn Tyr Gln Asn His Ala Val Tyr Leu Ala Asn Ile Ala Gln
             160                 165                 170 cat gct caa caa aat tgg gga atc cag ttt cag tca gtc gag gct ttt      624
His Ala Gln Gln Asn Trp Gly Ile Gln Phe Gln Ser Val Glu Ala Phe
         175                 180                 185 aac gag cct tcg tcg ggc tgg gga cct acc ggt aca caa gaa ggc tgc      672
Asn Glu Pro Ser Ser Gly Trp Gly Pro Thr Gly Thr Gln Glu Gly Cys
     190                 195                 200 cat ttt gcg gta tca acg atg gct acg gtt atc ggt tac ttg aac act      720
His Phe Ala Val Ser Thr Met Ala Thr Val Ile Gly Tyr Leu Asn Thr
205                 210                 215                 220
```

| | | |
|---|---|---|
| gag ctt gcg caa cgt gga cta tca tca ttt att tct gca tca gat gaa<br>Glu Leu Ala Gln Arg Gly Leu Ser Ser Phe Ile Ser Ala Ser Asp Glu<br>               225                   230               235 | | 768 |
| aca agt tac gac ctg gcc ata tca act tgg cag ggc cta ggc agc tct<br>Thr Ser Tyr Asp Leu Ala Ile Ser Thr Trp Gln Gly Leu Gly Ser Ser<br>               240                   245               250 | | 816 |
| gcc cag aac gct gtg aag cgt gtc aat gtt cat ggc tac cag ggc ggc<br>Ala Gln Asn Ala Val Lys Arg Val Asn Val His Gly Tyr Gln Gly Gly<br>               255                   260               265 | | 864 |
| ggc gga cga cgt gat acg ctt tat agc ctt gta agt caa gcc ggg aag<br>Gly Gly Arg Arg Asp Thr Leu Tyr Ser Leu Val Ser Gln Ala Gly Lys<br>        270                   275                   280 | | 912 |
| aga ctg tgg aac agt gaa tat ggc gat gca gat gca agt gga aaa tcg<br>Arg Leu Trp Asn Ser Glu Tyr Gly Asp Ala Asp Ala Ser Gly Lys Ser<br>285                   290                   295               300 | | 960 |
| atg tat aca aat ctg ctc ctt gat ttt acc tgg ctc cac cct acc gct<br>Met Tyr Thr Asn Leu Leu Leu Asp Phe Thr Trp Leu His Pro Thr Ala<br>               305                   310               315 | | 1008 |
| tgg gta tac tgg cag gca att gac ggt tca ggt tgg gga ctc atc gtt<br>Trp Val Tyr Trp Gln Ala Ile Asp Gly Ser Gly Trp Gly Leu Ile Val<br>                   320                   325               330 | | 1056 |
| ggc gat aat gat cag ttg acg ctt tca tcc gca agc act aag tac ttt<br>Gly Asp Asn Asp Gln Leu Thr Leu Ser Ser Ala Ser Thr Lys Tyr Phe<br>               335                   340               345 | | 1104 |
| gta ctg gcg caa tta act cgc cat atc agg ccc ggc atg cag atc ttg<br>Val Leu Ala Gln Leu Thr Arg His Ile Arg Pro Gly Met Gln Ile Leu<br>        350                   355                   360 | | 1152 |
| acc acc cct gat ggt aac act gtc gct gct tac gac tct ggc tct caa<br>Thr Thr Pro Asp Gly Asn Thr Val Ala Ala Tyr Asp Ser Gly Ser Gln<br>365                   370                   375               380 | | 1200 |
| aag ctc gtc att gtt gct gca aac tgg ggc agt gct cag act atc acc<br>Lys Leu Val Ile Val Ala Ala Asn Trp Gly Ser Ala Gln Thr Ile Thr<br>               385                   390               395 | | 1248 |
| ttt gat ctt act cgt gct aag act gct ggc agt aat ggt gca aca gtg<br>Phe Asp Leu Thr Arg Ala Lys Thr Ala Gly Ser Asn Gly Ala Thr Val<br>        400                   405                   410 | | 1296 |
| cca cga tgg agc acc caa aca agt ggt ggg gac caa tac aag agc tat<br>Pro Arg Trp Ser Thr Gln Thr Ser Gly Gly Asp Gln Tyr Lys Ser Tyr<br>               415                   420               425 | | 1344 |
| tcg gat aca aag atc aat aac ggg aaa ttc tct gtg tct ttt tct act<br>Ser Asp Thr Lys Ile Asn Asn Gly Lys Phe Ser Val Ser Phe Ser Thr<br>        430                   435                   440 | | 1392 |
| gga caa gtg cag aca ttt gag att agt ggt gtt gtg ctg aaa tga<br>Gly Gln Val Gln Thr Phe Glu Ile Ser Gly Val Val Leu Lys<br>445                   450                   455 | | 1437 |

<210> SEQ ID NO 2
<211> LENGTH: 478
<212> TYPE: PRT
<213> ORGANISM: Trichoderma harzianum

<400> SEQUENCE: 2

Met Arg Ser Ala Ile Thr Pro Ser Leu Ala Leu Ala Leu Leu Ser Gln
-20                 -15                 -10                  -5

Thr Ala Gly Ala Asp Thr Thr Leu Ser Ile Asp Pro Thr Ser Asn Trp
            -1   1               5                  10

Gly Thr Trp Glu Gly Trp Gly Val Ser Leu Ala Trp Trp Ala Lys Ala
        15                  20                  25

Phe Gly Asn Arg Asp Asp Leu Ala Asn Val Phe Phe Thr Arg Asn Asn
    30                  35                  40

```
Gln Val Ile Asn Gly Gln Asn Leu Pro Gly Leu Gly Phe Asn Ile Ala
 45                  50                  55                  60

Arg Tyr Asn Ala Gly Ala Cys Ser Thr Asn Thr Tyr Asn Gly Ser Ser
                 65                  70                  75

Met Val Val Ser Ser Ser Ile Lys Pro Ser Arg Gln Val Asp Gly Tyr
             80                  85                  90

Trp Leu Asp Trp Ala Ser Thr Asp Pro Ala Ser Ser Ser Trp Asn Trp
         95                 100                 105

Asn Val Asp Ala Asn Gln Arg Ala Met Leu Gln Lys Ala Lys Ala Asn
     110                 115                 120

Gly Ala Asn Ile Phe Glu Leu Phe Ser Asn Ser Pro Met Trp Trp Met
125                 130                 135                 140

Cys Leu Asn His Asn Pro Ser Gly Ser Gly Ser Ser Asp Asn Leu Gln
                145                 150                 155

Ser Trp Asn Tyr Gln Asn His Ala Val Tyr Leu Ala Asn Ile Ala Gln
            160                 165                 170

His Ala Gln Gln Asn Trp Gly Ile Gln Phe Gln Ser Val Glu Ala Phe
        175                 180                 185

Asn Glu Pro Ser Ser Gly Trp Gly Pro Thr Gly Thr Gln Glu Gly Cys
    190                 195                 200

His Phe Ala Val Ser Thr Met Ala Thr Val Ile Gly Tyr Leu Asn Thr
205                 210                 215                 220

Glu Leu Ala Gln Arg Gly Leu Ser Ser Phe Ile Ser Ala Ser Asp Glu
                225                 230                 235

Thr Ser Tyr Asp Leu Ala Ile Ser Thr Trp Gln Gly Leu Gly Ser Ser
            240                 245                 250

Ala Gln Asn Ala Val Lys Arg Val Asn Val His Gly Tyr Gln Gly Gly
        255                 260                 265

Gly Gly Arg Arg Asp Thr Leu Tyr Ser Leu Val Ser Gln Ala Gly Lys
    270                 275                 280

Arg Leu Trp Asn Ser Glu Tyr Gly Asp Ala Asp Ala Ser Gly Lys Ser
285                 290                 295                 300

Met Tyr Thr Asn Leu Leu Leu Asp Phe Thr Trp Leu His Pro Thr Ala
                305                 310                 315

Trp Val Tyr Trp Gln Ala Ile Asp Gly Ser Gly Trp Gly Leu Ile Val
            320                 325                 330

Gly Asp Asn Asp Gln Leu Thr Leu Ser Ser Ala Ser Thr Lys Tyr Phe
        335                 340                 345

Val Leu Ala Gln Leu Thr Arg His Ile Arg Pro Gly Met Gln Ile Leu
    350                 355                 360

Thr Thr Pro Asp Gly Asn Thr Val Ala Ala Tyr Asp Ser Gly Ser Gln
365                 370                 375                 380

Lys Leu Val Ile Val Ala Ala Asn Trp Gly Ser Ala Gln Thr Ile Thr
                385                 390                 395

Phe Asp Leu Thr Arg Ala Lys Thr Ala Gly Ser Asn Gly Ala Thr Val
            400                 405                 410

Pro Arg Trp Ser Thr Gln Thr Ser Gly Gly Asp Gln Tyr Lys Ser Tyr
        415                 420                 425

Ser Asp Thr Lys Ile Asn Asn Gly Lys Phe Ser Val Ser Phe Ser Thr
    430                 435                 440

Gly Gln Val Gln Thr Phe Glu Ile Ser Gly Val Val Leu Lys
445                 450                 455
```

<210> SEQ ID NO 3
<211> LENGTH: 43
<212> TYPE: DNA
<213> ORGANISM: Artificial Sequence
<220> FEATURE:
<223> OTHER INFORMATION: Primer

<400> SEQUENCE: 3
acacaactgg ggatccacca tgcgatcagc tattactcca tcg         43

<210> SEQ ID NO 4
<211> LENGTH: 38
<212> TYPE: DNA
<213> ORGANISM: Artificial Sequence
<220> FEATURE:
<223> OTHER INFORMATION: Primer

<400> SEQUENCE: 4
agatctcgag aagcttatca tttcagcaca acaccact                38

<210> SEQ ID NO 5
<211> LENGTH: 20
<212> TYPE: DNA
<213> ORGANISM: Artificial Sequence
<220> FEATURE:
<223> OTHER INFORMATION: Primer 8653

<400> SEQUENCE: 5
gcaagggatg ccatgcttgg                                    20

<210> SEQ ID NO 6
<211> LENGTH: 19
<212> TYPE: DNA
<213> ORGANISM: Artificial Sequence
<220> FEATURE:
<223> OTHER INFORMATION: Primer 8654

<400> SEQUENCE: 6
catataacca attgccctc                                     19

<210> SEQ ID NO 7
<211> LENGTH: 269
<212> TYPE: PRT
<213> ORGANISM: Bacillus  lentus (subtilisin 309)

<400> SEQUENCE: 7

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

```
Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

<210> SEQ ID NO 8
<211> LENGTH: 275
<212> TYPE: PRT
<213> ORGANISM: Bacillus amyloliquefaciens

<400> SEQUENCE: 8

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
        50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
                100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
        130                 135                 140

Ser Gly Val Val Val Ala Ala Ala Gly Asn Glu Gly Thr Ser Gly Ser
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
                180                 185                 190

Gly Pro Glu Leu Asp Val Met Ala Pro Gly Val Ser Ile Gln Ser Thr
                195                 200                 205

Leu Pro Gly Asn Lys Tyr Gly Ala Tyr Asn Gly Thr Ser Met Ala Ser
        210                 215                 220

Pro His Val Ala Gly Ala Ala Ala Leu Ile Leu Ser Lys His Pro Asn
```

```
225                 230                 235                 240
Trp Thr Asn Thr Gln Val Arg Ser Ser Leu Glu Asn Thr Thr Thr Lys
                245                 250                 255
Leu Gly Asp Ser Phe Tyr Tyr Gly Lys Gly Leu Ile Asn Val Gln Ala
            260                 265                 270
Ala Ala Gln
        275
```